(12) United States Patent
Crisp et al.

(10) Patent No.: US 9,936,686 B2
(45) Date of Patent: Apr. 10, 2018

(54) METHOD AND APPARATUS FOR THE MANAGEMENT OF A SOIL PEST

(71) Applicant: Lisi Global, LLC, Richland, WA (US)

(72) Inventors: Jason D. Crisp, Newark, DE (US); Ekaterini Riga, Newark, DE (US); Gordon J. McComb, Kennewick, WA (US)

(73) Assignee: Lisi Globa, LLC, Richland, WA (US)

( * ) Notice: Subject to any disclaimer, the term of this patent is extended or adjusted under 35 U.S.C. 154(b) by 527 days.

(21) Appl. No.: 14/462,733

(22) Filed: Aug. 19, 2014

(65) Prior Publication Data
US 2016/0050902 A1 Feb. 25, 2016

(51) Int. Cl.
| A01M 17/00 | (2006.01) |
| A01M 1/22 | (2006.01) |
| A01M 19/00 | (2006.01) |
| G01N 33/24 | (2006.01) |
| G01N 27/22 | (2006.01) |

(52) U.S. Cl.
CPC ............ *A01M 17/00* (2013.01); *A01M 1/223* (2013.01); *A01M 19/00* (2013.01); *G01N 27/22* (2013.01); *G01N 33/24* (2013.01)

(58) Field of Classification Search
CPC .. A01M 21/0046; A01M 1/223; A01M 19/00; A01M 1/00; A01M 1/20; A01M 1/22; A01M 1/226; A01M 17/00; A01M 21/00; A01M 21/046; A01M 43/112
USPC ............... 43/112, 132.1, 124; 47/1.3, 1.01 R
See application file for complete search history.

(56) References Cited

U.S. PATENT DOCUMENTS

| 1,737,866 | A |   | 12/1929 | Roe |
| 2,429,412 | A |   | 10/1947 | Keller |
| 2,588,561 | A |   | 3/1952 | Opp et al. |
| 2,750,712 | A |   | 6/1956 | Rainey |
| 3,559,337 | A | * | 2/1971 | Marcoux et al. ... A01M 21/046 126/271.1 |
| 4,428,150 | A | * | 1/1984 | Geiersbach ......... A01M 21/046 363/64 |
| 4,758,318 | A |   | 7/1988 | Yoshida |

(Continued)

FOREIGN PATENT DOCUMENTS

| CN | 2699673 Y | 5/2005 |
| CN | 101622983 A | 1/2010 |

(Continued)

OTHER PUBLICATIONS

E. Riga et al., "Electrophysiological Responses of Males of the Potato Cyst Nematodes . . . ," Article, 1996, pp. 239-246, Cambridge University Press.

(Continued)

*Primary Examiner* — Cassandra H Davis
(74) *Attorney, Agent, or Firm* — Wells St. John P.S.

(57) ABSTRACT

A method and apparatus for the management of a soil pest is disclosed and which includes a source of high voltage electricity; at least one capacitor for storing the high voltage electricity; a multiplicity of electrodes inserted into a soil location having a soil pest to be managed, and an electrical switch which is controllably opened and closed so as to form a pulse of electricity which is passed through the soil location and between the electrodes so as to effect the management of the soil pest.

25 Claims, 18 Drawing Sheets

(56) References Cited

U.S. PATENT DOCUMENTS

| | | | |
|---|---|---|---|
| 4,817,331 A * | 4/1989 | Podsiadly | A01M 19/00 43/1 |
| 5,141,059 A | 8/1992 | Marsh | |
| 5,210,719 A * | 5/1993 | Lawrence | A01M 1/223 331/178 |
| 5,271,470 A | 12/1993 | King et al. | |
| 5,435,096 A * | 7/1995 | Nekomoto | A01M 1/223 43/112 |
| 5,949,636 A | 9/1999 | Johnson et al. | |
| 6,223,464 B1 * | 5/2001 | Nekomoto | A01M 1/223 43/112 |
| 6,237,278 B1 * | 5/2001 | Persson | A01M 21/046 47/1.3 |
| 6,320,197 B1 | 11/2001 | Smit et al. | |
| 2003/0150156 A1 * | 8/2003 | Flagler | A01M 19/00 47/1.3 |
| 2006/0024195 A1 | 2/2006 | Lagunas-Solar et al. | |
| 2017/0202202 A1 | 7/2017 | Crisp et al. | |

FOREIGN PATENT DOCUMENTS

| | | |
|---|---|---|
| CN | 103896369 A | 7/2014 |
| WO | WO 9717830 | 5/1997 |
| WO | WO 2009064065 A1 | 5/2009 |
| WO | PCT/US2015/043980 | 11/2015 |
| WO | PCT/US2015/043980 | 2/2017 |

OTHER PUBLICATIONS

E. Riga et al., "Investigation of the Chemosensory Function of Amphids . . . ," Article, 1995, pp. 347-351, Cambridge University Press.
E. Riga et al., "Electrophysiological Analysis of the Response of Males . . . ," Article,1996, pp. 493-498, E. J. Brill, Leiden.
E. Riga et al., "Electrophysiological Analysis of the Response of Males . . . ," Article, 1997, pp. 311-316, Cambridge University Press.
PCT Search Report dated Nov. 9, 2015.
Kris Lambert et al., "Introduction to Plant-Parasitic Nematodes," Article, 2002, University of Illinois, Urbana, IL.
Pouya Rezai et al., "Effect of Pulse Direct Current Signals on Electrotactic Movement of Nematodes . . . ," Article, 2011, American Institute of Physics.
Robin Meadows, "Researchers Develop Alternatives to Methyl Bromide Fumigation," Publication, 2013, California Agriculture.
W.T. Crow, PHD, "Biology Derived Alternatives to Nemacur," Article, 2005, pp. 147-150, GCM.
Dr. Katerina Jordan, "Navigating Nematodes," Article, 2007, pp. 18-21, GreenMaster.
Paul Koch, "Where Did All the Nematodes Go?," Article, 2007, pp. 25-26, The Grass Roots.
Fields E. Caveness et al., "Nematode Electrocution," Article, 1970, pp. 298-304, Journal of Nematology.
Han-Sheng Chuang et al., "Dielectrophoresis of Caenorhabditis Elegans," Article, 2010, pp. 599-604, Royal Society of Chemistry.
J.M. Nicol et al., "Current Nematode Threats to World Agriculture," Book, 2011, pp. 21-43, Springer Science+Business Media B.V.
Charles Overstreet, "Nemotode Management Changing in Golf Greens," Article, 2007, pp. 15-16, Tee to Green.

K.R. Barker et al., "Plant and Soil Nematodes: Societal Impact and Focus for the Future," Article, 1994, pp. 127-137, vol. 26, No. 2, Journal of Nematology, Raleigh, NC.
USDA Agricultural Research Service, National Program 303-Plant Diseases Action Plan 2012-2016, Journal, 2013, pp. 1-17, USDA.
Pouya Rezai et al., "Co-Relation of Cellular and Behavioral Responses of . . . ", Article, 2012, pp. 1609-1611, Miniaturized Systems for Chemistry and Life Sciences Conference, Japan.
J.P. Walrond et al., "Excitatory and Inhibitory Activity in the Dorsal Musculature of the Nematode . . . ," Article, 1985, pp. 16-22, Society for Neuroscience, Wisconsin.
Bert Lear et al., "Electrical Tests on Nematodes," Article, 1955, pp. 9 & 14, California Agriculture.
Tjitske Heida et al., "Investigating Membrane Breakdown of Neuronal Cells Exposed . . . ," Article, 2002, pp. 1195-1203, vol. 49, No. 10, IEEE.
Roland N. Perry et al., "Electrophysiological Analysis of Sensory Response of Parasitic Nematodes," Article, 1995, pp. 61-69, vol. 25, No. 2, Japanese Journal of Nematology.
Ekaterini Riga et al., "Electrophysiological Responses of Male Potato Cyst Nematodes," Article, 1997, pp. 417-428, vol. 23, No. 2, Plenum Publishing Corp.
Bamgbose, "Economic Importance of Fungi in Agriculture", available online at http://www.academia.edu/4498319/ Economic_Importance_of_Fungi_in_Agriculture_full_text, Nov. 2012, 13 pages.
Bost, "Commercial Vegetable Disease Control Guide", University of Tennessee, available online at https://extension.tennessee. edu/ publications/documents/W141.pdf, 2015, 50 pages.
Brent et al., "Fungicide Resistance in Crop Pathogens: How Can it be Managed?", 2nd Edition, revised, Crop Life International, available online at http://www.frac.info/docs/default-source/publications/monographs/monograph-1.pdf, 2007, 60 pages.
Godoy et al. "Brazilian Soybean Pest Management", Research Information Ltd., available online at https://ainfo. cnptia.embrapa. br/digital/bitstream/item/126257/1/Godoy-et-al.-2015.pdf, Jun. 2015, 5 pages.
Life of Plant, "Ascomycetes", Plant Life, available online at http:// lifeofplant.blogspot.com/2011/12/ascomycetes.html, Dec. 2011 (printed Mar. 1, 2017), 3 pages.
Meyer et al., "Using Soil-Applied Fungicides to Manage . . . ", Plant Disease vol. 97, No. 1, available online at https://www.researchgate. net /publication/277486532_Using_Soil-Applied_Fungicides_to_Manage_Phytophthora_Crown_and_ Root_Rot_on_Summer_ Squash, Aug. 2012, pp. 107-112.
Moore et al., "Fungal Diseases and the Loss of World Agricultural Production", 21st Century Guidebook to Fungi, available online at http://www.davidmoore.org.uk/ 21st_Century_Guidebook_to_Fungi_PLATINUM/Ch14_01.htm, Dec. 17, 2016, 3 pages.
Roberts et al., "Fungicides", Chapter 16 of Recognition and Management of Pesticide Poisonings, 6th Edition, EPA, available online at http://npic.orst.edu/RMPP/rmpp_ch16.pdf, 2013, pp. 143-160.
Saalau, "Fungicides and How to Use Them Effectively", Iowa State University Extension Outreach Horticulture and Home Pest News, Jun. 1, 2011, available online at http://hortnews.extension.iastate. edu/2011/6-1/fungicides.html, 1 page.
Williams et al., "Fungal and Fungal-Like Diseases of Plants", Ohio State University Exension, Feb. 9, 2017, available online at http:// ohioline.osu.edu/factsheet/plpath-gen-7, 4 pages.

* cited by examiner

METHOD AND APPARATUS FOR THE MANAGEMENT OF A SOIL PEST

TECHNICAL FIELD

The present invention relates to a method and apparatus for the management of a soil pest, and more specifically to a methodology and apparatus which delivers a predetermined amount of electrical current to a soil treatment area, and which is effective in reducing the deleterious effects of nematodes and similar organisms on plants which are planted, and growing in the same treatment area.

BACKGROUND OF THE INVENTION

Members of the phylum nematoda [round worms] have been in existence for an estimated one billion years. This makes them one of the most ancient and diverse types of animals now available for study on the earth. These organisms are thought to have evolved from simple animals. Two nematode classes—the Chromadorida and Enoplea diverged so long ago that it is difficult to know the exact age of the two lineages of the phylum.

Nematodes are multi-cellular organisms in the group Ecdysozoa. These are organisms that can shed their cuticle. Also included in this group with nematodes are insects, arachnids and crustaceans. Most literature suggests that based upon molecular phylogenic analysis, it would appear that nematodes have evolved their ability to parasitize animals and plants several times during their evolution. What appears clear is that nematodes have evolved to fill almost every conceivable niche on earth that contains some amount of water. Most nematodes are free-living, and feed on bacteria, fungi, protozoans and other nematodes, and many others are parasites for animals or plants.

The U.S. Department of Agriculture and other agencies have long known and reported that plant parasitic nematodes are recognized as one of the greatest threats to crops throughout the world. In fact, nematodes, alone, or in combination with other soil microorganisms have been found to attack almost every part of the plant, including roots, stems, leaves, fruits and seeds. In one recent report, a survey of more than 35 states regarding various crops indicated that nematode-derived losses reached upwardly to nearly 25%. Nematologists, who are studying the effects of nematodes, put this percentage considerably higher. In fact, one investigator reported that the difficulty with assessing nematode impact is that the damage resulting from a nematode infestation is often less obvious than that caused by other pests or diseases. In fact, losses that result from nematodes may not necessarily be a consequence of direct cell death, but may derive from other, more insidious aspects, such as interference with the root system, and reducing their efficiency in terms of access and uptake of nutrients, and water, and other similar effects. One commentator noted that nematodes are often described as the unseen enemy in crop production, and may be responsible for an estimated 100 billion dollars in global crop losses per year. Those skilled in the art have recognized that once a nematode population gets established, they have been nearly impossible to eradicate. Typically such infestations have been managed by crop rotation, introducing genetic crop resistance, and the use of chemicals and biologicals. With increasingly larger world populations projected by 2050, and later, an increase in food demand, in the order of 75%, is anticipated. Significant improvements, therefore, are necessary in terms of resource use efficiency, and crop yields, if these food demands are going to be met. However, this cannot be achieved if nematode infestations continue at their current levels.

The problems associated with nematode infestations, and the damage to crop yields are well known, and various devices, and methodology have been developed, through the years, in an attempt to manage these pests so as to increase the quality and amount of crops which are harvested. The literature has reported that fumigants, sometimes in conjunction with other chemical mitigants, have been the traditional means for controlling nematodes, heretofore. Currently, fumigant application is the dominant means for controlling nematodes in the United States, France, Japan, Italy and Spain. Fumigant sales account for 45% of the total nematocides sales globally. However, the high cost of the available fumigants has restricted their use to high value crops in countries where these admittedly toxic products can be applied safely and effectively. Many countries have severely restricted the use of fumigants, or completely banned them altogether. The consequence for farmers in these jurisdictions where fumigants have been restricted has been that they have very limited choices of products to control nematodes effectively, and consequently crop yields are lower. One of the most effective fumigants for nematodes is Methyl Bromide. Many farmers have recognized this soil fumigant is just short of a miracle for the management of this pest. Methyl Bromide has been shown, in a single treatment before planting, to control nematodes, other plant diseases, and weeds. However, Methyl Bromide is also recognized as a health and environmental hazard, and is being phased out under an international ban. Other fumigants are under testing by the U.S. Department of Agriculture, and other agencies. However, the recent literature does not show any of these fumigants have reached the level of efficacy that Methyl Bromide has. Investigators attempting to control soil pests, such as nematodes and the like, have sought other methods beyond that of fumigation and which is the common methodology used at this time. In view of this situation, a long felt need for other commercially viable, and environmentally friendly treatments for the management of a soil pest, like Nematodes, has been sought by assorted agricultural produce producers.

The Office's attention is directed to U.S. Pat. No. 1,737,866, which appears to be one of the earliest known patents, and which describes a method and apparatus for the practice of agriculture. This patent discloses the use of a plow device, and wherein the plow includes harrow discs or other oppositely charged implements, which act as electrodes, and wherein a source of electricity is passed into the plow-shares or harrow discs. The electrically energized harrow discs are reported, in this reference, to be effective in destroying germinating seeds, and inhibit the activity of insects, worms, larvae and eggs that are in the soil, thus practically exterminating them. The Office's attention is also directed to U.S. Pat. No. 2,750,712, to Rainey, and which relates to another apparatus and methodology for applying electrical current to a soil treatment area, and which is intended to destroy undesired weeds, grass and insect life by the application of electrical current to the insects, and undesired plants during cultivation. Still another attempt to apply electrical current to a cultivated area is seen in U.S. Plant Application Publication No. 2003/0150156 A1 to Flagler, et al. Again, this particular reference discloses a method and apparatus for eradicating nematodes, and other soil borne organisms, to a depth of up to several feet. This published U.S. patent application discloses the use of specially-shaped, electrically conductive metal shanks that are pulled through the soil profile by a tractor, or other suitable vehicle. Examples, of other prior art references which disclose the application of electrical current to a soil treatment area for the control of weeds, insects, nematodes, and the like, are also seen in U.S. Pat. Nos. 2,429,412; 2,588,561; 4,758,318; and 6,237,278 to name but a few.

While numerous attempts have been made to identify a means for controlling nematode infestations through the use of assorted means, including electrical charges passed through the soil, these attempts have not been successful or widely adopted by farmers and growers for a number of different reasons, including, but not limited to, the cost associated with utilizing the methodology or devices; the slow speed with which an area of soil can be effectively treated; and the resulting low efficacy of such treatments, in relative comparison to commercially available fumigants which have been used heretofore, such as Methyl Bromide. Notwithstanding the persistent problem of decreasing crop yields, and further in view of the international ban on fumigants such as Methyl Bromide, these previous prior art attempts at managing soil pests using electrical current have largely been ignored, or have been considered not particularly effective or commercially attractive to the degree necessary to meet the nematode threat now facing growers. While much research has been conducted regarding alternative means to control soil pests without the use of fumigants, and which have demonstrated, environmental and other health hazards, a long felt need has persisted that an alternative to fumigation must be identified if food growers are going to have any likelihood of increasing crop yields to meet the world food needs of an increasing population in the not too distant future, while avoiding collateral environmental damage.

A method and apparatus for the management of a soil pest is the subject matter of the present application.

SUMMARY OF THE INVENTION

A first aspect of the present invention relates to a method for the management of a soil pest, and which includes providing a source of high voltage electricity having a predetermined capacitance; electrically coupling the source of high voltage electricity having the predetermined capacitance with a soil location having a soil pest which requires management; and supplying the source of high voltage electricity having the predetermined capacitance to the soil in a predetermined number of pulses to effect an in-situ management of the soil pest at the soil location.

Still another aspect of the present invention relates to a method for the management of a soil pest, which includes providing a source of high voltage electricity; providing a plurality of spaced electrodes each having a given length dimension, and which are oriented in a predetermined, spaced relationship, one relative to the other, and orienting the spaced electrodes in electrical discharging relation relative to a soil location having a soil pest to be managed; providing a capacitor and which is electrically coupled with the source of the high voltage electricity, and storing the source of the high voltage electricity in the capacitor so as to form a source of high voltage electricity having a predetermined capacitance; providing a high voltage solid state electrical switch which is electrically coupled with the source of high voltage electricity having the predetermined capacitance, and which is stored in the capacitor, and wherein the high voltage solid state electrical switch is further electrically coupled with each of the spaced electrodes, and wherein the high voltage solid state electrical switch can be rendered electrically open so as to facilitate a storage of the source of high voltage electricity in the capacitor, and electrically closed so as to facilitate an electrical discharge of the capacitor and the subsequent delivery of the source of the high voltage electricity having the predetermined capacitance to the respective plurality of spaced electrodes; providing an electrical switch driver which is electrically coupled with the high voltage solid state electrical switch, and wherein the high voltage solid state electrical switch, when actuated, is effective in causing the high voltage solid state electrical switch to be rendered either electrically open, or electrically closed; providing an isolation transformer which is electrically coupled with both the source of the high voltage electricity having the predetermined capacitance, and with the plurality of spaced electrodes which are oriented in electrical discharging relation relative to the soil location, and operating the isolation transformer in a manner so as to effect a transmission of the high voltage electricity having the predetermined capacitance through the soil location, and between the adjacent spaced electrodes, and to impede the dissipation of the high voltage electricity having the predetermined capacitance into the soil at the soil location; providing a controller which is coupled in controlling relation relative to the electrical switch driver, and which is effective in rendering the high voltage solid state electrical switch electrically opened and closed; and repeatedly rendering the electrical switch driver operable to facilitate an electrical opening and closing of the high voltage solid state electrical switch and so forming a multiplicity of pulses of electricity which are delivered to the plurality of electrodes, and which are oriented in electrical discharging relation relative to the soil location, and wherein the plurality of electrical pulses facilitate a reduction in an adverse soil pest effect at the soil location of greater than about 5%.

Still another aspect of the present invention relates to an apparatus for managing a soil pest, and which includes a source of high voltage electricity having a predetermined capacitance; an isolation transformer electrically coupled with the source of the high voltage electricity having the predetermined capacitance; a plurality of spaced electrodes which are located in electrical contact with a soil location which has a soil pest to be managed, and wherein the isolation transformer is electrically coupled to the respective spaced electrodes; a capacitor which is electrically coupled with the source of high voltage electricity having a predetermined capacitance, and with the plurality of spaced electrodes, and wherein the capacitor can store the source of high voltage electricity having the predetermined capacitance, and subsequently discharge the previously stored high voltage electricity having the predetermined capacitance to the plurality of spaced electrodes; and a high voltage electrical switch which is electrically coupled to the capacitor, and which further can be rendered electrically opened, and closed in a predetermined manner, so as to produce a predetermined electrical pulse which is electrically transmitted to the respective plurality of spaced electrodes, and across the soil location, and wherein the electrical pulse delivers at least about 2 joules of electricity per cubic centimeter of soil which is located at the soil location so as to facilitate a management of the soil pest.

These and other aspects of the present invention will be discussed in greater detail, hereinafter.

BRIEF DESCRIPTION OF THE DRAWINGS

Preferred embodiments of the invention are described below with reference to the following accompanying drawings.

FIG. 4A is a greatly magnified view of a portion of a soil location to be treated, and which depicts one type of soil pest to be managed by the disclosed methodology.

DETAILED DESCRIPTION OF THE PREFERRED EMBODIMENTS

This disclosure of the invention is submitted in furtherance of the constitutional purposes of the U.S. Patent laws "to promote the progress of science in useful art" [Article I, Section 8].

Figure 1:
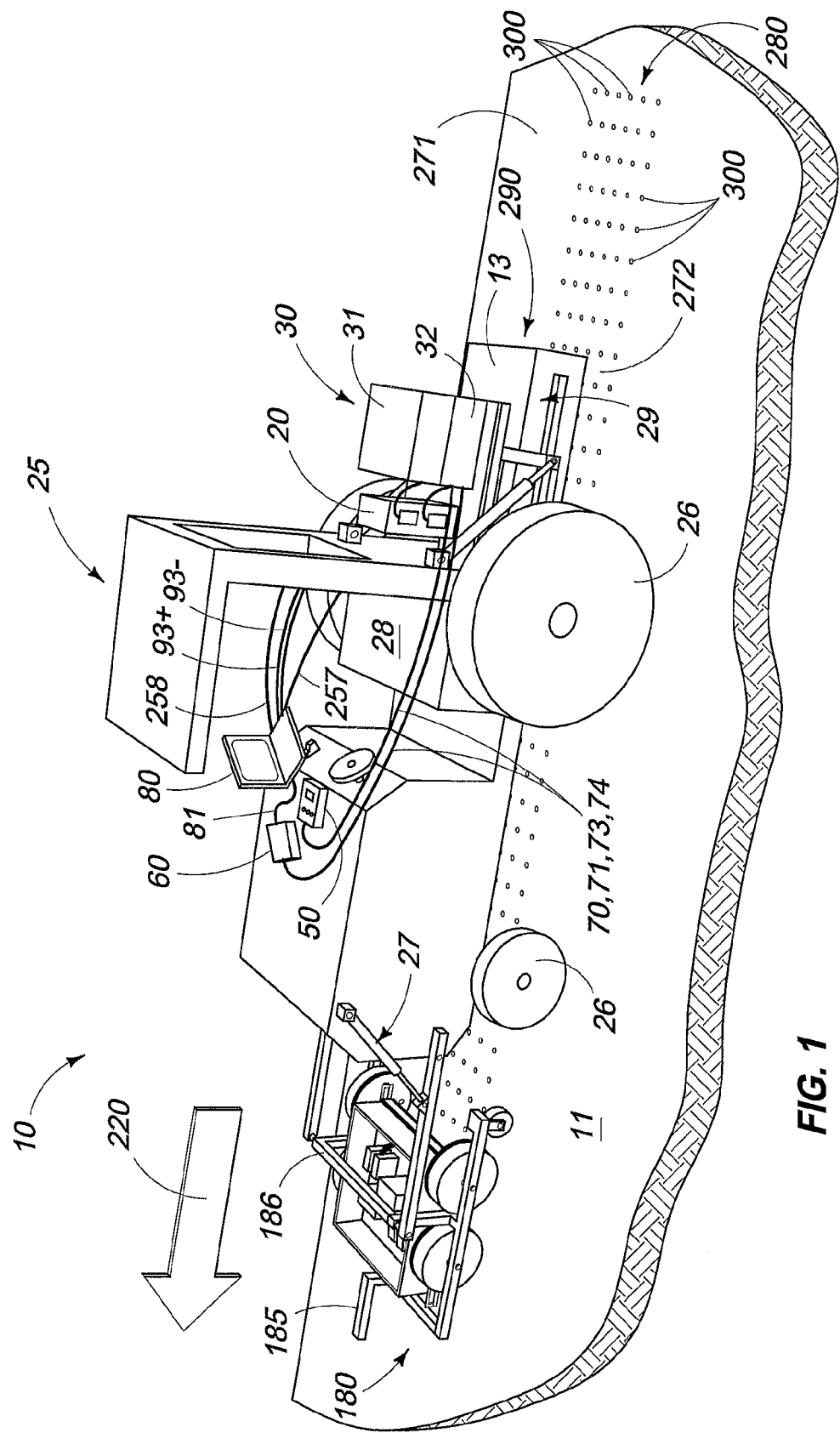
FIG. 1 is a greatly simplified, perspective, side elevation view of the present invention, and which is shown in a typical operational arrangement, and while treating an underlying soil region.
Figure 2:
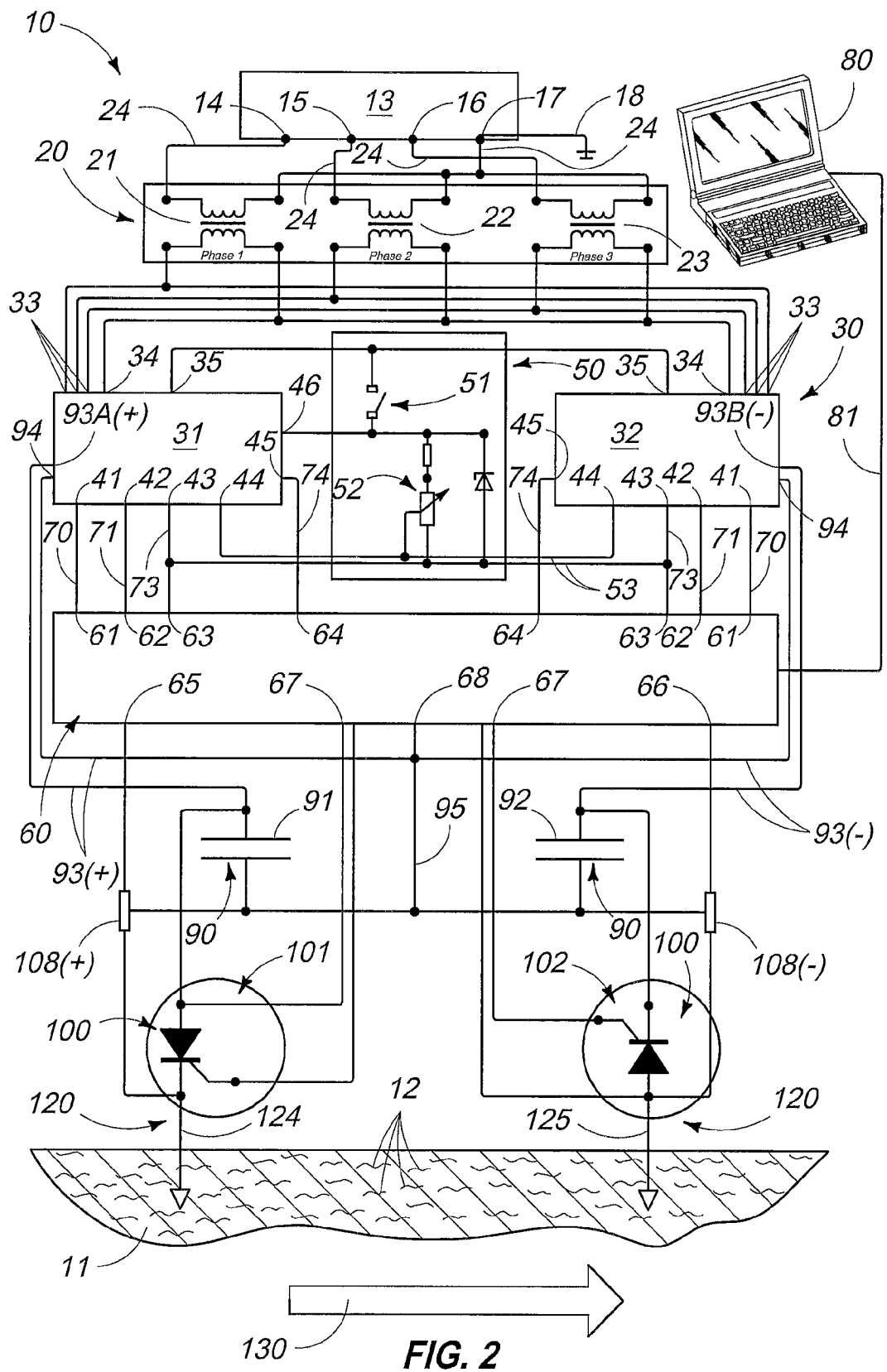
FIG. 2 is a highly simplified, electrical schematic showing one form of an overall operational, electrical arrangement for implementing the methodology of the present invention.
Figure 3:
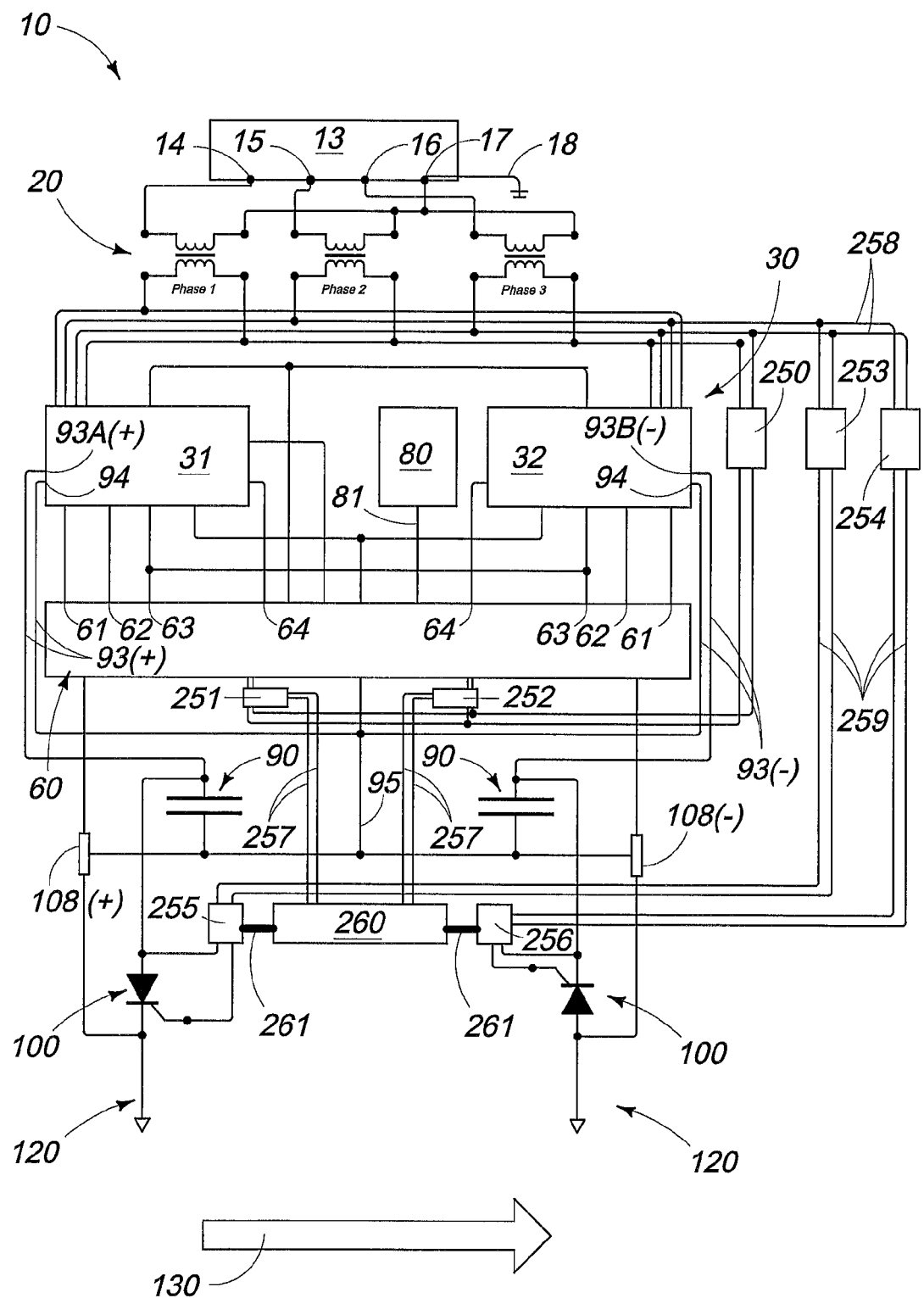
FIG. 3 is a second, highly simplified, electrical schematic for implementing the teachings of the present invention.
Figure 4:
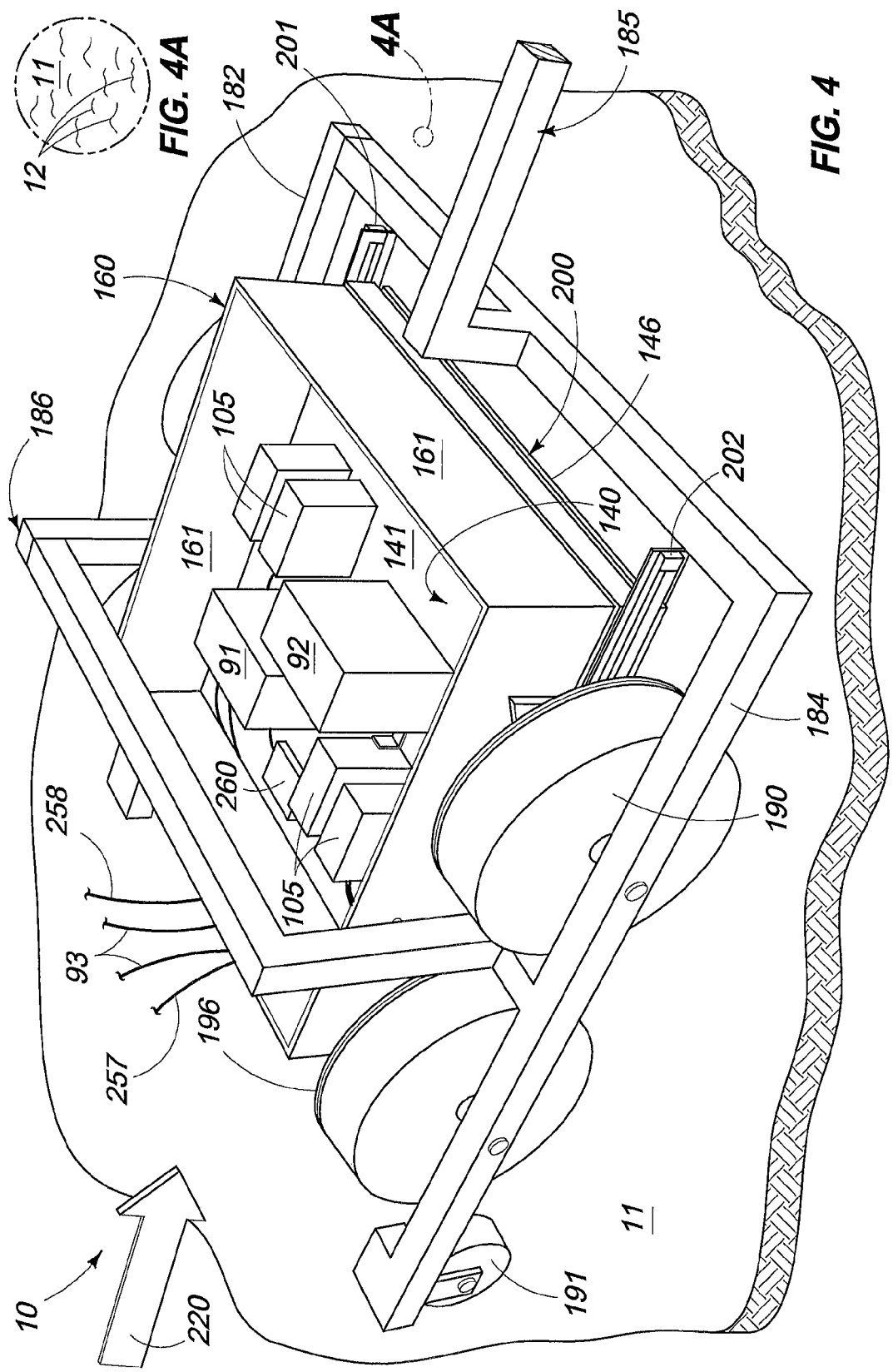
FIG. 4 is a perspective, side elevation view of a greatly simplified apparatus, which implements the methodology for the management of a soil pest of the present invention.

The method and apparatus for the management of a soil pest of the present invention is best seen by reference to FIG. 1 and following. The method and apparatus, which will generally be indicated by the numeral 10, is useful for treating a given soil location and which is generally indicated by the numeral 11, in FIG. 1, and following. The soil location 11 includes a soil pest to be managed, and which is generally indicated by the numeral 12 in FIG. 4A. The soil pest, as depicted, is shown as worms, or nematodes, which are only fancifully depicted in that view, but these same soil pests may further include other organisms such as earthworms; wax worms; crickets; and various nematodes, as described earlier, and which are harmful to plants growing in the soil location 11 to be treated. The method of the present invention 10 includes a first step of providing a source of high voltage electricity having a predetermined capacitance 13 (FIGS. 2 and 3). In the methodology and apparatus 10, as described, hereinafter, the first step includes the provision of a three-phase, 208 volt AC generator 290, which may be mounted in one possible form of the invention at a fixed location; or in another possible embodiment the generator may be mounted for movement across the soil location 11 (FIG. 1), in order to supply the source of electricity 13 to an accompanying treatment apparatus, which will be described below. The source of high voltage electricity 13 includes a phase A, B and C, indicated by the numerals 14, 15 and 16, respectively. The source of the high voltage electricity further includes a neutral terminal 17, and an accompanying electrical ground 18. This step of providing the high voltage electricity 13, having a predetermined capacitance comprises generating a source of high voltage DC electricity, having a voltage in a range of about 1 kV to about 100 kV; an amperage of about 50 amps to about 50 kA; a frequency of about 1 Hz to about 100 Hz; and a capacitance of about 1 uF to about 1,000 uF. With regard to the method as described above, the soil location 11, has a soil electrical conductivity, which lies in a range of about 100 to about 2,500 Micro Siemens per cubic centimeter of soil at the soil location 11. Still further, the soil pest to be managed at the soil location 11 is selected from the group comprising Tylenchomorpha nematodes; Diptherophorina nematodes; and Dorylaminda nematodes; and a selected neurological response of the soil pest 12 to be managed at the soil location and which is affected by the methodology as described hereinafter, comprises a motility; sensory and/or an autonomic response of the soil pest 12 to be managed. With regard to the present methodology 10, the method and apparatus, as described hereinafter, is employed to deter or inhibit an adverse soil pest effect 12 at the soil location 11, and which may include, but is not limited to, root galling and/or root infestation of a plant which is planted at the soil location 11, and which is caused by the action of the soil pest 12. As should be understood, the adverse soil pest effect decreases a plant vigor; a crop yield; and/or lowers the production quality of a plant, which is affected by the soil pest, at the soil location where the plant is being grown.

Referring still to FIG. 2, the method and apparatus 10 of the present invention includes an isolation transformer, which is generally indicated by the numeral 20. The isolation transformer 20 operates in a manner which is well known in the art. The isolation transformer 20 includes phase A, phase B and phase C isolation transformer components, and which are indicated by the numerals 21, 22 and 23, respectively. As illustrated in FIG. 2, the respective individual isolation transformer components 21, 22 and 23 are electrically coupled to the source of high voltage electricity 13, by electrical conduits 24, which directly couple the phase A, phase B and phase C isolation transformer components to the phase A, phase B and phase C and ground 14, 15, 16 and 18, as previously described.

As seen in FIG. 1, the method and apparatus 10 as described is propelled over the soil location 11, in one form of the invention, by a tractor or similar vehicle 25. The tractor is of conventional design having earth engaging wheels 26; a forwardly oriented lifting arrangement 27; and an operator's position 28. The tractor 25 has a trailing storage region 29 for supporting components of the apparatus which will be described in further detail, below.

The method and apparatus 10 of the present invention (FIG. 2) includes a high voltage switching power supply, here generally indicated by the numerals 30 in FIG. 2. The high voltage switching power supply 30 includes a first and a second switching power supply 31 and 32, respectively, which cooperatively and electrically are coupled together in order to provide the benefits as will be described, below. The respective first and second high voltage switching power supplies 31 and 32 each have a group of three-phase, 208 volt, power terminals 33, which are electrically coupled to the respective phase A, phase B and phase C, isolation transformer components 21, 22 and 23, respectively, as illustrated in FIG. 2. Still further, the respective high voltage switching power supplies 30 each have a neutral terminal 34, which is connected to the neutral terminal 17, and to the ground 18, as illustrated. Further, each of the respective first and second high voltage switching power supplies 31 and 32, has a high voltage power on/off terminal 35, which are respectively electrically coupled together as illustrated. The high voltage switching power supplies 30 are operable to quickly electrically charge capacitors, as will be described, hereinafter. In the form of the invention as shown, the respective high voltage, switching power supplies have an average charging rate of about 4,000 Joules per second, at the rated output voltage. Further, each of the high voltage switching power supplies 31 and 32 have power output terminals labeled 93(A)(Positive Terminal) and 93 (B)(Negative Terminal) respectively; and yet another electrical terminal 94. Electrical conduits labeled 93(+) and 93(−) are each electrically coupled to the high voltage switching power supplies, and with each of the downstream capacitors, as will be described, below. Additionally, the respective first and second high voltage switching power supplies 31 and 32 each have an Analog A terminal, indicated by the numeral 41, and an Analog V terminal, which is indicated by the numeral 42. Further, each of the aforementioned power supplies also has a Reference terminal 43; and a V program terminal 44. Additionally, each of the aforementioned switching power supplies has an Inhibit terminal 45. As illustrated in the drawings, the first high voltage switching power supply 31 has a 15 volt direct current output terminal 46. As best illustrated in FIG. 2, the V program terminals 44 are electrically coupled together. Similarly the reference terminals 43 are electrically coupled together.

As seen in FIG. 2, and following, the method and apparatus of the present invention 10 includes a high voltage control switch, which is generally indicated by the numeral 50, and which is used for controlling and energizing the high voltage switching power supplies 31 and 32, respectively. The high voltage control switch 50, which can be triggered remotely by a controller, as will be described in greater detail, below, includes an electrical switch 51, and further includes a potentiometer 52. Both of these are labeled in FIG. 2. The high voltage control switch 50 for controlling the respective high voltage switching power supplies 31 and 32, respectively, are electrically coupled to each of the high voltage switching power supplies by means of electrical conduits 53, and which are electrically coupled to the terminals 43 and 44, respectively, and which are found on each of the high voltage switching power supplies 31 and 32.

The method and apparatus 10 of the present invention (FIG. 2) includes a pulse control and wave form monitoring unit, which is generally indicated by the numeral 60, in FIG. 2. The pulse control and wave form monitoring unit is electrically coupled to the aforementioned high voltage switching power supplies 30, and high voltage control switch 50 for controlling the aforementioned power supplies 30. The pulse control and wave form monitoring unit 60 includes a pair of Analog A terminals, which are generally indicated by the numeral 61. Still further, the same pulse control, and wave form monitoring unit 60 includes a pair of Analog V terminals 62. This same assembly 60 also includes a pair of Reference terminals 63; and a pair of Inhibit terminals which are generally indicated by the numeral 64. Additionally, the pulse control and wave form monitoring unit 60 includes an electrically positive pulse monitoring terminal 65; and an electrically negative pulse monitoring terminal 66. Still further, the pulse control and wave form monitoring unit 60 includes a pair of Trigger terminals 67, and a Reference monitoring terminal 68. As seen in the drawings, a pair of electrical conduits 70, individually couple the Analog A terminals 41, and 61, together. Still further, a pair of electrical conduits 71, individually electrically couple the Analog V terminals 42 and 62 together. Still further, a pair of electrical conduits 73, individually couple the respective reference terminals 43 and 63 together. Additionally, and as seen in FIG. 2, a pair of electrical conduits 74 individually couple the Inhibit terminals 45 and 64, together.

The method and apparatus 10, as best seen in FIG. 2, includes a controller which is generally indicated by the numeral 80, and which is herein illustrated as a conventional laptop computer 80, and which is further coupled in controlling relation relative to the pulse control, and wave form monitoring unit 60 by means of a USB cable 81. Of course this same electrical coupling could be achieved by a wireless connection if desired. The controller 80, or laptop computer, provides a convenient means for an operator, not shown, to monitor the operation of the apparatus, which implements the methodology 10 of the present invention, and which will be described in greater detail below. Electrically coupled to the pulse control, and wave form monitoring unit 60 is a pair of capacitors, which are generally indicated by the numeral 90. The pair of capacitors include a first capacitor 91, and a second capacitor 92. The capacitors are of conventional design, and have the ability to store electricity, which is generated by the high voltage switching power supplies 30, which are, again, electrically coupled with the source of high voltage electricity 13. The respective capacitors 90 are operable to be electrically charged, and then discharged during a predetermined period so as to provide pulses of electricity, as will be described below, which are then passed through the soil location 11 to achieve the benefits of the invention, as will be described in later detail in this Application. As illustrated, the first and second capacitors 91 and 92, are electrically coupled to the power output terminals 93(A); 93(B); and 94 of each of the respective high voltage switching power supplies 30 by a pair of electrical conduits 93 (Positive), and 93(Negative), in order to receive the electrical current to charge same. The pair of electrical conduits 93 (Positive and Negative) are also coupled by means of an electrical conduit 95 to the Reference terminal 68, and electrically terminals 94, as provided on the pulse control and wave form monitoring unit 60.

The method and apparatus 10 includes a pair of high voltage, solid-state electrical switches 100, which are individually electrically coupled with each of the capacitors 91 and 92, respectively. The pair of high voltage solid-state electrical switches include a first high-voltage switch 101; and a second high voltage switch 102. Additionally, the apparatus 10 includes first and second pulse boards 255 and 256, respectively, (FIG. 3), and which are individually and respectively coupled to the first and second high voltage, solid-state switches 101 and 102, respectively. As seen in the drawings (FIG. 5), individual heat sinks 105, are positioned adjacent, and in heat removing relation relative to, the first and second high voltage, solid-state electrical switches 101 and 102 respectively. The heat sinks are used to dissipate heat energy generated during the operation of the high voltage, solid-state electrical switches 101 and 102, respectively. The high voltage, solid-state electrical switches comprise silicon controlled rectifiers (SCR), as illustrated. These are well known in the art and are employed to quickly electrically open and close in order to release stored electrical energy from the previously charged capacitors 91 and 92, respectively, in order to achieve a discharge of pulsed electricity as will be described, below, and which travels between adjacent electrodes, in order to implement the methodology for controlling a soil pest at the soil location 11. As seen in the drawings (FIGS. 3 and 5), a pair of voltage supply assemblies 253, and 254 are provided and are electrically coupled 259 and energize the individual pulse boards 255, and 256, and in the manner which is described, below. Electrically coupled to each of the monitoring connections, 65 and 66 are individual high voltage monitoring probes 108(+) and 108(−), respectively (FIGS. 2 and 3).

Referring now to FIG. 2, and following, it will be seen that the method and apparatus 10 of the present invention includes a multiplicity of electrodes which are generally indicated by the numeral 120, and which are further operable to be placed or inserted within the soil location 11, to a given depth, and wherein, when the apparatus is rendered operational, periodic pulses of electricity of a given magnitude, and duration, are passed through the soil location 11, to be treated, in order to achieve the benefits of the present methodology. In this regard, the electrodes 120 (FIG. 6) include an elongated main body 121 which can be repeatedly, and forcibly inserted within the soil location 11, to a given depth, by the operation of the apparatus as will be further described, hereinafter. This repeated forcible insertion, and then removal or withdrawal of the respective electrodes 120 takes place with a minimum of disturbance to the soil location 11. The individual electrodes have a main body 121, with a proximal end 122, and which is coupled to an electrical bus as will be described, below, and further has a distal end 123, and which is located a given distance below the surface of the soil location 11. The respective plurality of electrodes 120 include both electrically positive electrodes 124 (FIG. 7); and electrically negative electrodes 125. When rendered operational, previously stored electricity in the respective capacitors 90, passes into the individual electrodes by means of the electrical bus as will be described, hereinafter, and then moves between the positive and negative electrodes 124 and 125 to achieve the benefits of the invention. The pulse of electricity 130 which is generated by the electrical discharge of the capacitors 91 and 92 respectively is represented by the numeral 130 as seen in FIG. 2 hereinafter.

Figure 5:
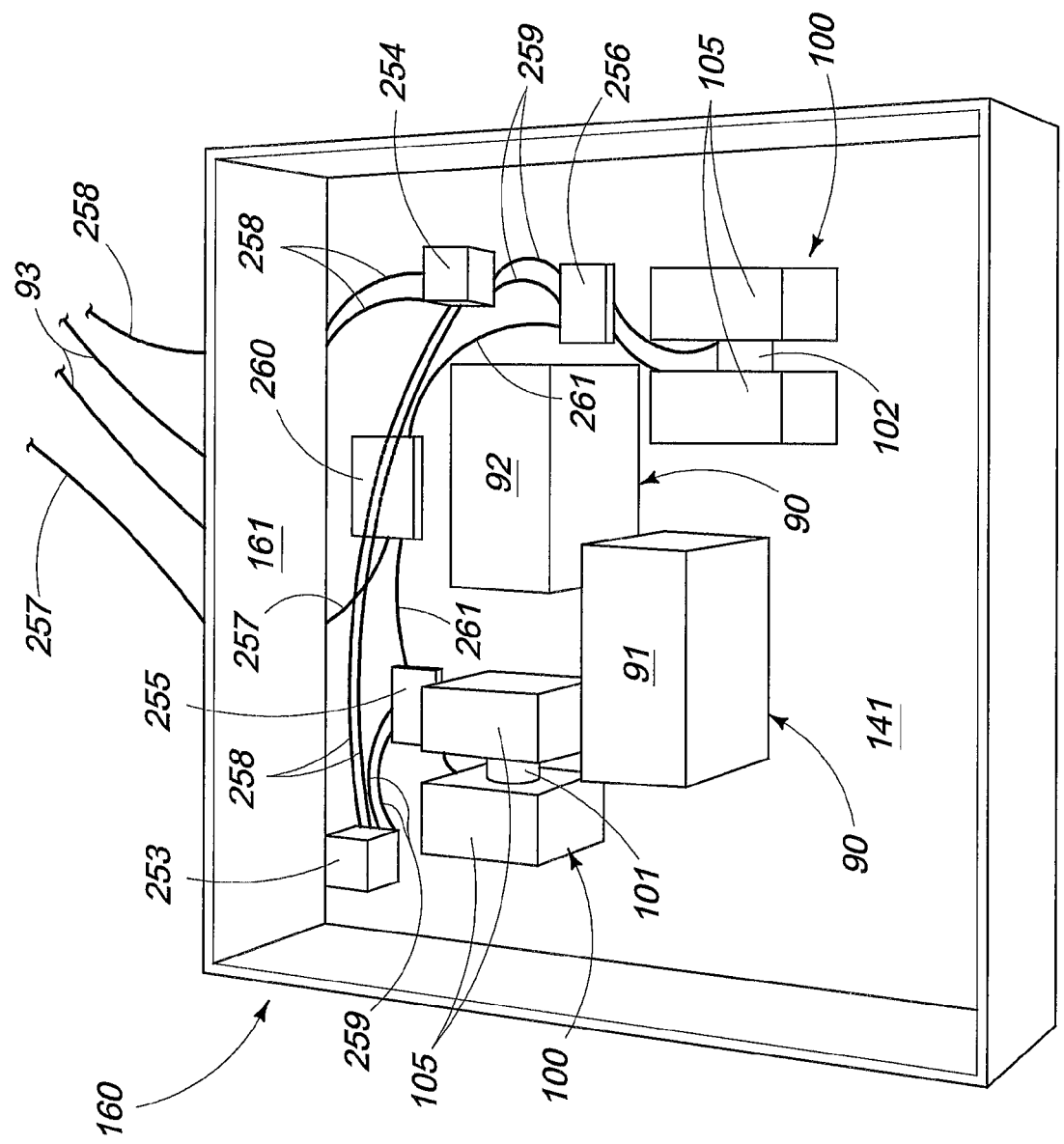
FIG. 5 is a fragmentary, top plan view of one possible physical arrangement of several electrical components, which implement the methodology of the present invention.

Referring now to FIG. 3, an alternative embodiment of the invention is seen. In this rather simplified illustration, earlier numerical designations used in FIG. 2 indicate similar structures in this drawing. As will be recognized in this greatly simplified drawing, the source of high voltage electricity 13; isolation transformer 20; and high voltage switching power supplies 30 remain the same, and are electrically coupled in a manner that is similar to that which was earlier described. Again, a controller 80 is provided, and which can be used by an operator, not shown, who will be operating the invention 10. A pulse control and wave form monitoring unit 60 is provided. In addition, capacitors 90, are repeatedly charged, and then discharged by the actions of the high voltage solid state switches 100, as illustrated. In this form of the invention, a voltage supply assembly 250 is provided, and which receives 110 volts AC from the isolation transformer 20, and which further supplies a resulting 24 volts DC to downstream first and second solid state relays 251, and 252 respectively. The solid state relays are electrically coupled to the pulse control and wave form monitoring unit 60. Additional voltage supply assembles 253 and 254, each convert 208 volt AC electrical power from the isolation transformer 20 via electrical conduits which are labeled 258 into 11 volts AC and supply to individual positive and negative electrical pulse printed circuit boards 255 and 256, respectively via electrical conduits 259. The first and second solid state relays 251, and 252 are coupled to the electric pulse board controller 260 by pairs of electrical conduits which are labeled 257. The arrangement as seen in FIGS. 3 and 5 includes an electrical pulse board controller 260, and which is electrically coupled 257 with the respective solid state relays 251 and 252, respectively. The pulse board controller is controllably coupled by way of an optical fiber, or light pipe 261, with each of the respective electrical pulse boards 255 and 256. When energized, the pulse board controller 260 is operable to cause the respective pulse boards to activate the respective solid state electrical switches 100, in a manner so as to generate the predetermined electrical pulses 130. As earlier described, these electrical pulses 130 are delivered to the electrodes 120, and then is subsequently delivered through the soil location 11, so as to manage the soil pest 12.

Figure 6:
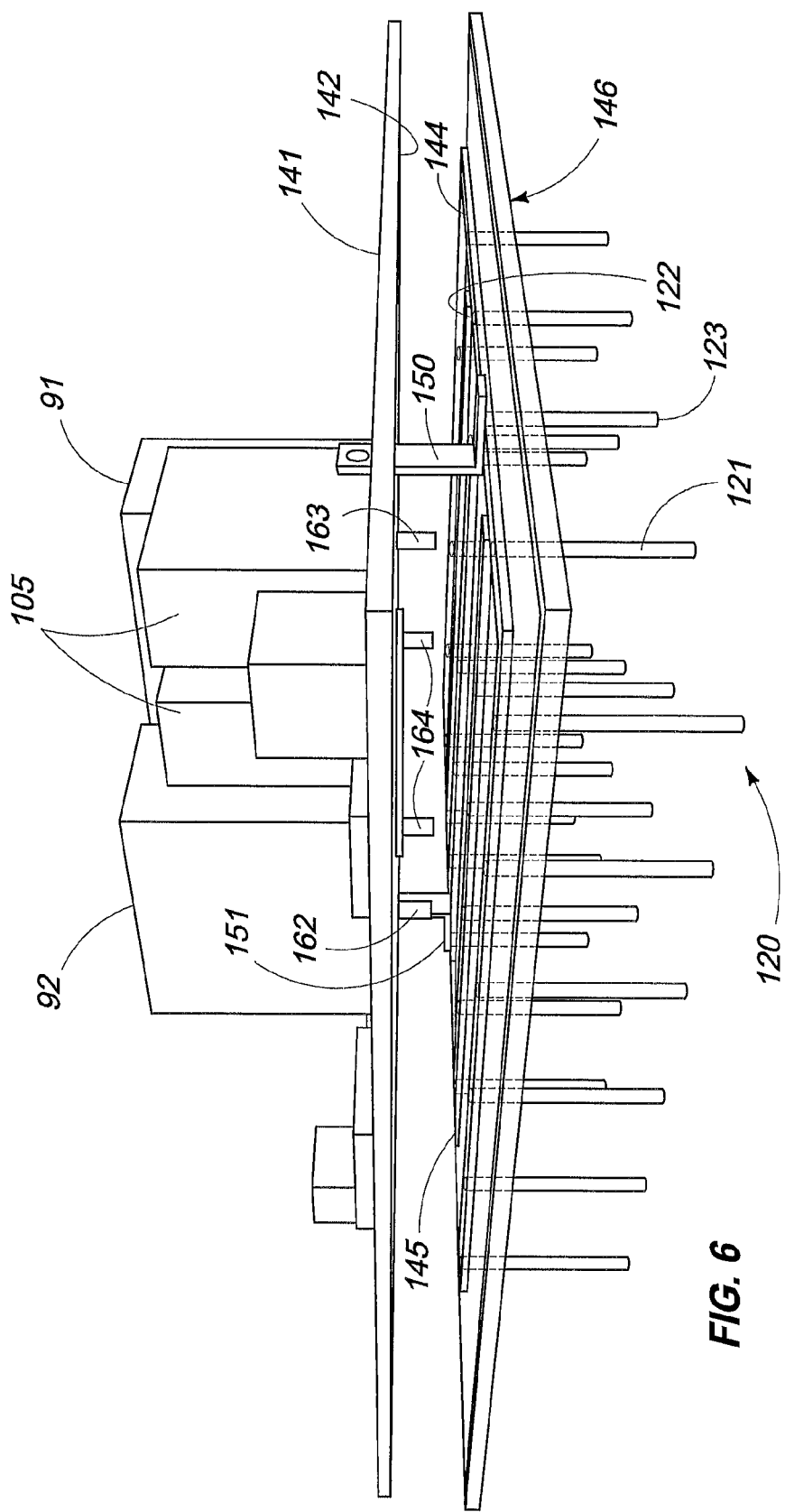
FIG. 6 is a fragmentary, perspective, exploded, side elevation view of several electronic components, which implement the methodology of the present invention.
Figure 7:
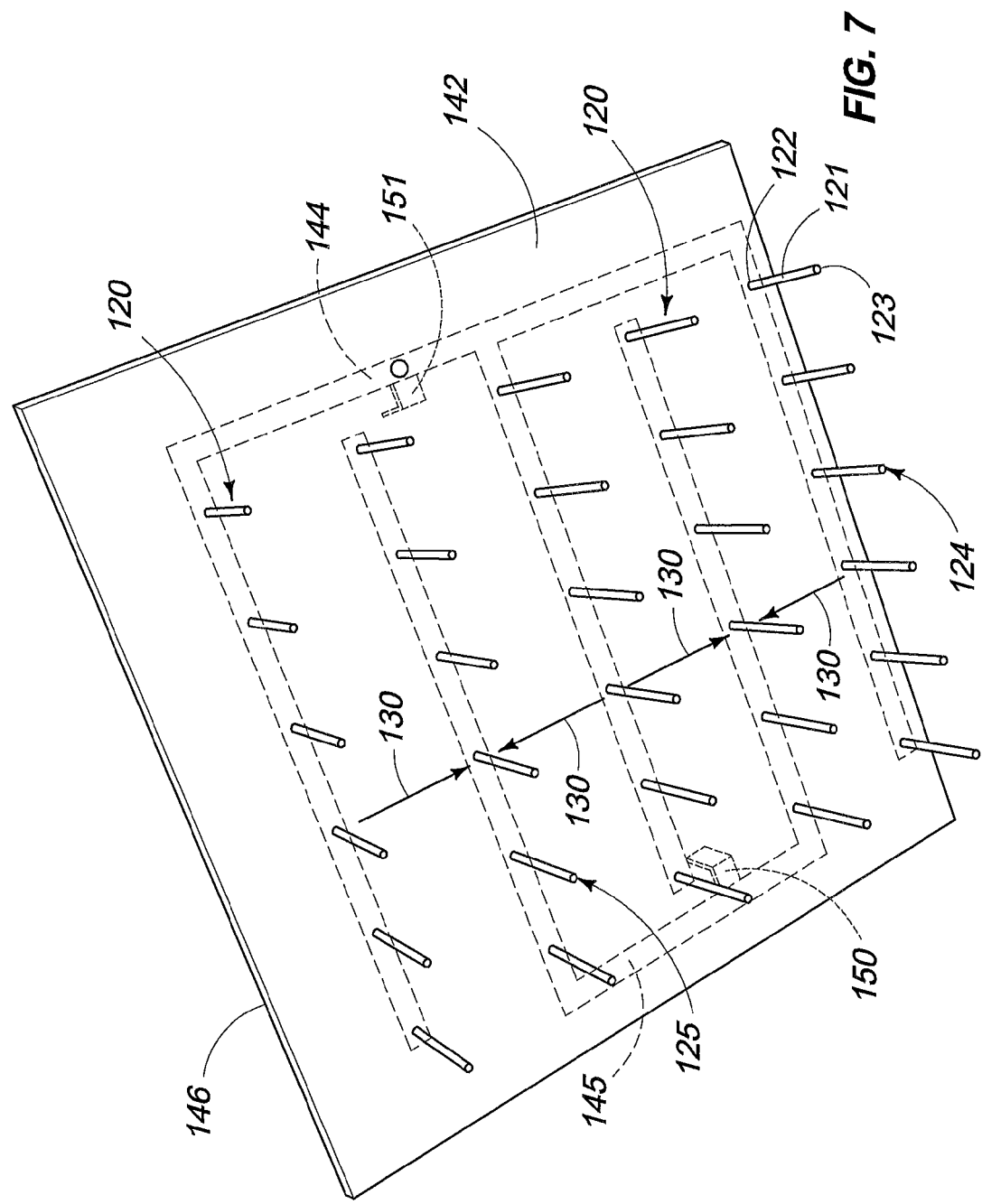
FIG. 7 is a fragmentary, bottom, plan view of a non-conductive supporting surface, and which shows a multiplicity of spaced electrodes, which further are positioned in a given array, and are utilized in the present invention.

As seen in the drawings (FIG. 4 and following), the present method and apparatus, which are generally indicated by the numeral 10, includes a non-conductive electrical platform which is generally indicated by the numeral 140. The non-conductive platform has a top surface 141, and upon which the electrical components such as the capacitors 91 and 92 are attached; and an opposite bottom surface 142 (FIG. 6). Still further, first and second electrically conductive pathways 144, and 145, are mounted on top of electrically nonconductive support member 146 as illustrated. Non-conductive spacing elements 143 (FIG. 10) are mounted on the top surface of electrically nonconductive support member 146. The spacing elements 143 locate the platform 140, and non-conductive support member 146 in spaced relation, one, relative to the other. As should be understood, the respective proximal ends 123 of the individual electrodes 120 are received through the non-conductive support member 146, and are electrically coupled 122 to the electrically conductive pathways 144 and 145 respectively. The electrodes 120 are further positioned in predetermined, spaced relation along the respective first and second electrical pathways, and are spaced a given distance apart so as to form an electrode array, and wherein the respective electrodes have a given spacing in order to achieve the benefits of the present invention as will be described, hereinafter (FIGS. 6 and 7). Individual electrically conductive bus bars which are generally indicated by the numeral 150 and 151, respectively (FIG. 7), individually couple the respective first and second electrical pathways 144 and 145 to the electrical components, as previously described, and which will be discussed in greater detail, below. Once assembled the platform 140 and non-conductive support member 146 move in unison, together, in the fashion as described, hereinafter.

Figure 8:
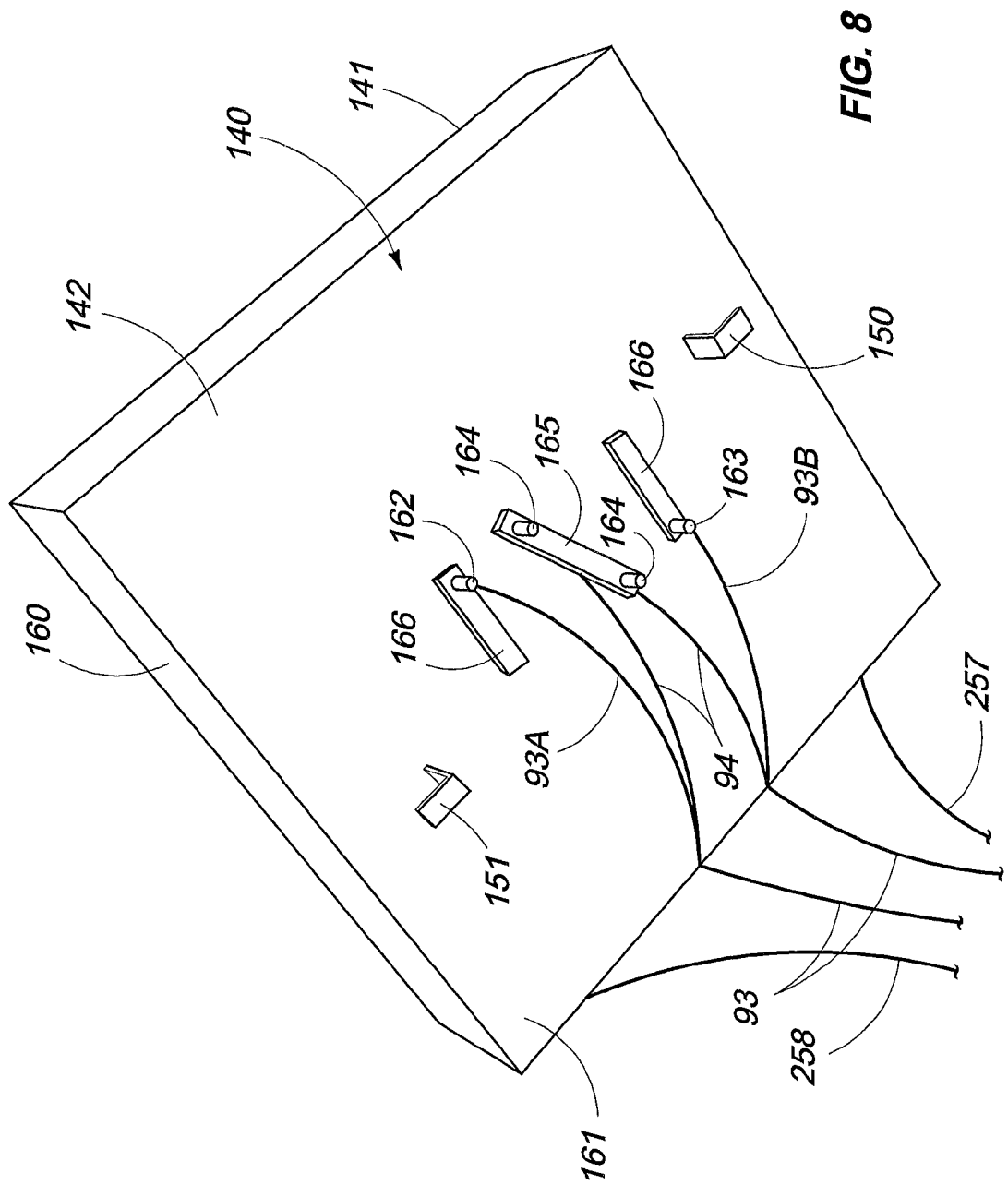
FIG. 8 is a plan view of a moveable platform, and which is employed in the methodology of the present invention.

Referring now to FIGS. 4, 5, 7 and 8, and again referring to the non-conductive supporting surface 146, and platform 140, the present apparatus 10 for implementing the methodology includes a housing 160 which is mounted on the top surface 141 of the non-conductive platform 140. The housing 160 has multiple, substantially vertically oriented sidewalls 161, and which enclose or define a cavity for receiving the electrical components as earlier described. As seen in FIG. 8, extending through the top and bottom surfaces 141 and 142, are first and second capacitor posts 162 and 163, respectively, and which are individually electrically coupled to the respective capacitors 91 and 92, respectively. Still further the individual capacitors 91 and 92 each have common electrical posts which are indicated by the numeral 164, and which extend through the top and bottom surfaces 141 and 142, respectively. An electrical pathway 165 electrically couples the common posts 164, together. As seen in FIG. 8, an electrical pathway 165 is provided, and which again couples the common posts 164 together. Still further, an electrical pathway 166 is provided (FIG. 8), and which extend upwardly through 142 & 141 to further electrically couple the individual first and second capacitor posts 162 and 163, respectively, to the earlier mentioned individual high voltage solid state switches 101 and 102, respectively, and which were discussed, above.

Figure 9:
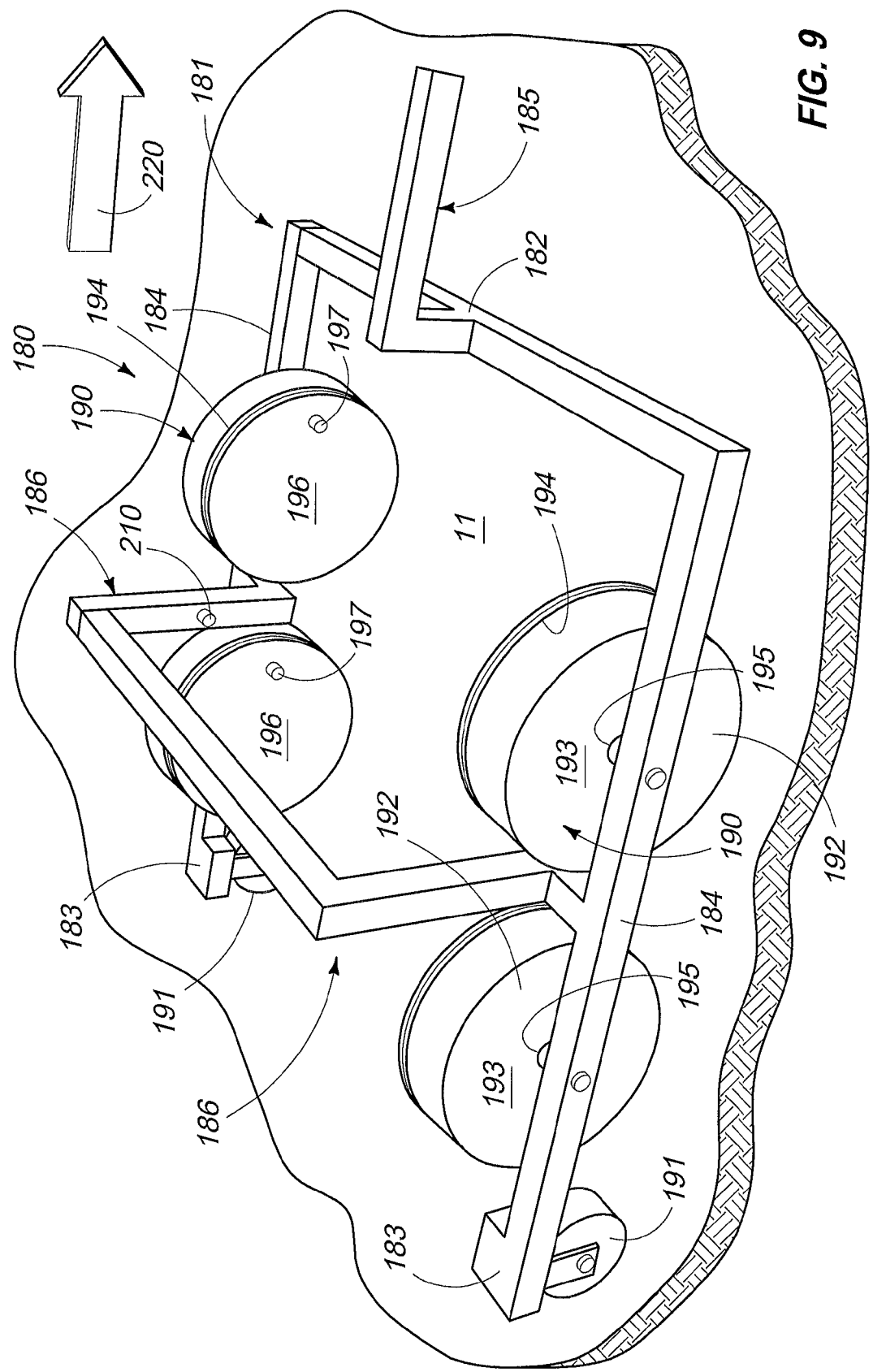
FIG. 9 is a greatly simplified view of an earth traversing vehicle or carriage, with some surfaces removed, and which is employed in the methodology of the present invention.

Referring now to FIG. 9, a feature of the present apparatus 10 for implementing the methodology is shown. As seen in this view, an earth traversing vehicle or carriage 180, is generally shown, and which further is supported for rolling engagement over the soil location 11 having the soil pest 12 to be managed. The earth traversing vehicle 180 has a supporting frame 181 which moves in a spaced relationship over the face of the earth. The earth traversing vehicle, and more specifically the supporting frame 181 has a first, or proximal end 182; and a second, or distal end 183. The supporting frame 181 is defined, at least in part, by a pair of laterally disposed and spaced, substantially parallel frame members 184. Still further, the lateral frame members 184 are held together in predetermined spaced relation by a manual maneuvering handle or yoke 185. This structure permits a user to maneuver or otherwise orient the frame 181 in a position so as to be effectively coupled to the tractor 25. Still further, and mounted on, and extending upwardly relative to the lateral frame members 184 is a transversely disposed and vertically extending platform guidance member 186 which is operable to matingly cooperate with the non conductive support member 146 as earlier described, in order to define a path of movement for the non-conductive supporting surface 146, and which is carrying the plurality of electrodes 120 in the array, and platform 140 by way of non-conductive spacing elements (not shown) as seen in FIG. 6. The lifting arrangement 27 for the tractor 25 is coupled in force transmitting relation relative to the platform guidance member 186 as seen in FIG. 1.

As seen in FIG. 9, the earth traversing vehicle or carriage 180 is held in rolling engagement relative to the soil requiring treatment 11 by means of a plurality of earth engaging wheels 190. The earth traversing vehicle 180 further includes a pair of inwardly disposed landing or castor wheels 191, and which are mounted on the distal end 183 of the supporting frame 181 and which work in conjunction with the manual maneuvering yoke 185 when de-coupled from the tractor 25. As illustrated, the earth engaging wheels 90 are mounted in pairs on the opposite lateral frame members 184, and are located on opposite sides of the respective, transversely disposed, and vertically extending platform guidance members 186. The earth engaging wheels 190 have a main body 192 which has an outside facing surface 193, and an opposite inside facing surface 194. An axle 195 renders the respective earth engaging wheels 190 rotatable relative to the respective lateral frame members 184. Rigid discs 196 cover at least in part, the inside facing surfaces 194 of the earth engaging wheels 190, and individual platform engaging posts 197 are positioned in predetermined orientations on the rigid discs 196, and the main body 192, and upon rotation of the earth engaging wheels 190, the non-conductive support member 146 as will be described, hereinafter, will move upwardly and downwardly relative to the soil region requiring treatment 11, and which is positioned, therebelow, the earth traversing vehicle 180.

Figure 10:
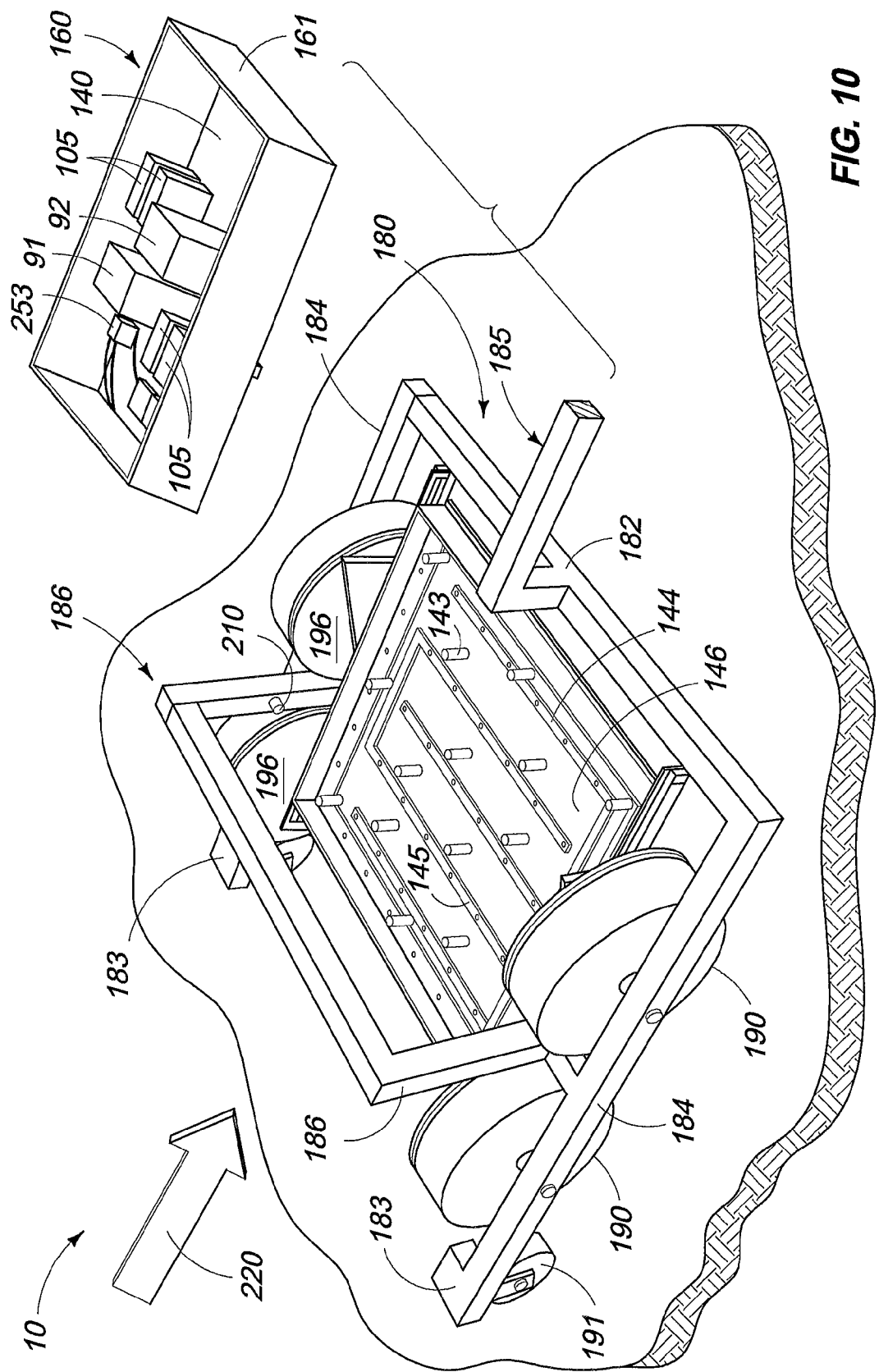
FIG. 10 is a perspective, partially exploded, side elevation view of an earth traversing vehicle carrying a movable platform, and which forms a feature of the present invention.
Figure 11:
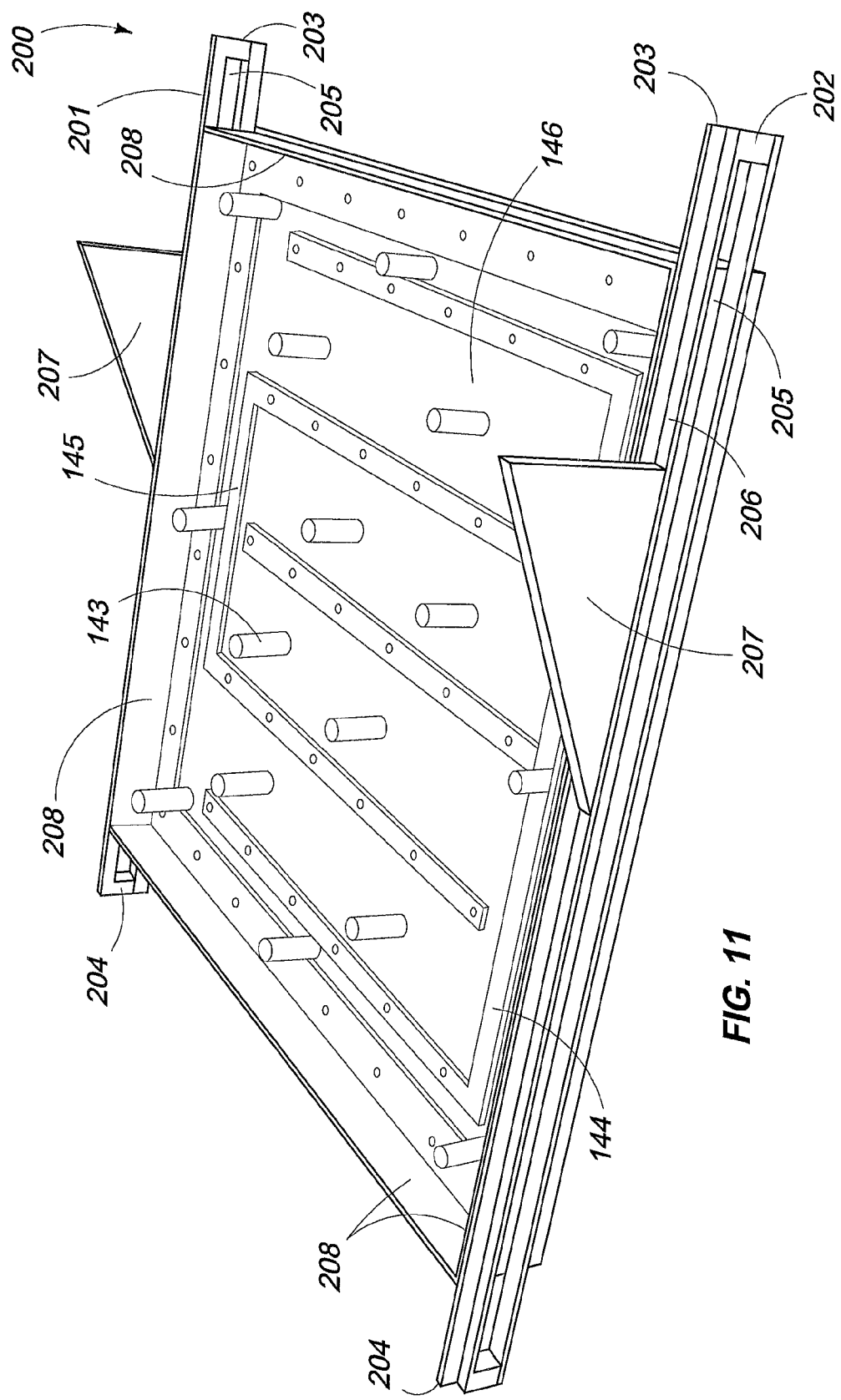
FIG. 11 is a fragmentary, perspective, side elevation view of a movable platform which forms a feature of the present invention.

Referring now to FIGS. 10 and 11, and as should be understood, the non-conductive support member 146 is rendered movable along a substantially vertically disposed path of travel, upwardly and downwardly, relative to the underlying soil treatment area 11, and which is located, therebeneath, the earth traversing vehicle 180 by a platform movement assembly which is generally indicated by the numeral 200. For ease in understanding the invention, 10, the housing 160, along with platform 140 and the mounted capacitors etc is removed in FIG. 11, and following, and only the non-conductive support member 146 is illustrated. However, it should be understood that the housing 160, along with platform 140 and the mounted capacitors etc, and the underlying non-conductive support member 146, (and through which the electrodes 120 extend, and are respectively electrically coupled to the first and second electrical pathways 144, and 145) move together, and in unison, along the aforementioned, vertical path of travel by the action of the platform movement assembly 200. In this regard, the non-conductive support member 146 has secured atop and along the outer perimeter a structural vertical member 208, thereto, a pair of laterally disposed first and second rail members 201 and 202, respectively, and which, form a portion of the platform movement assembly 200, and which are further operable to carry the non-conductive support member 146 in a direction towards, and away from, the soil treatment area 11. As can be seen, the first and second rail members 201 and 202, respectively, are positioned on opposite sides of the non-conductive support member 146, and are disposed in substantially parallel, spaced relationship, one relative to the other. The respective first and second rail members have opposite first and second ends 203 and 204, respectively, and which extend forwardly and rearwardly relative to the platform movement assembly 200. As can be seen in FIG. 11, a longitudinally extending channel 205 is formed in, and extends between the first and second ends 203 and 204 respectively. The individual channels are operable to engage, and receive for movement therein the individual platform engaging posts 197, and which are mounted on the rigid discs 196. As seen in FIG. 11, the respective first and second rail members 201 and 202, respectively, have an upwardly facing surface 206. Mounted on each of the upwardly facing surfaces is a rail engagement surface or member 207, and which is operable to cooperate in the manner as will be described, hereinafter, with the transversely disposed, and vertically extending platform guidance member 186 which is affixed to the respective lateral frame members 184 of the supporting frame 181.

Figure 18:
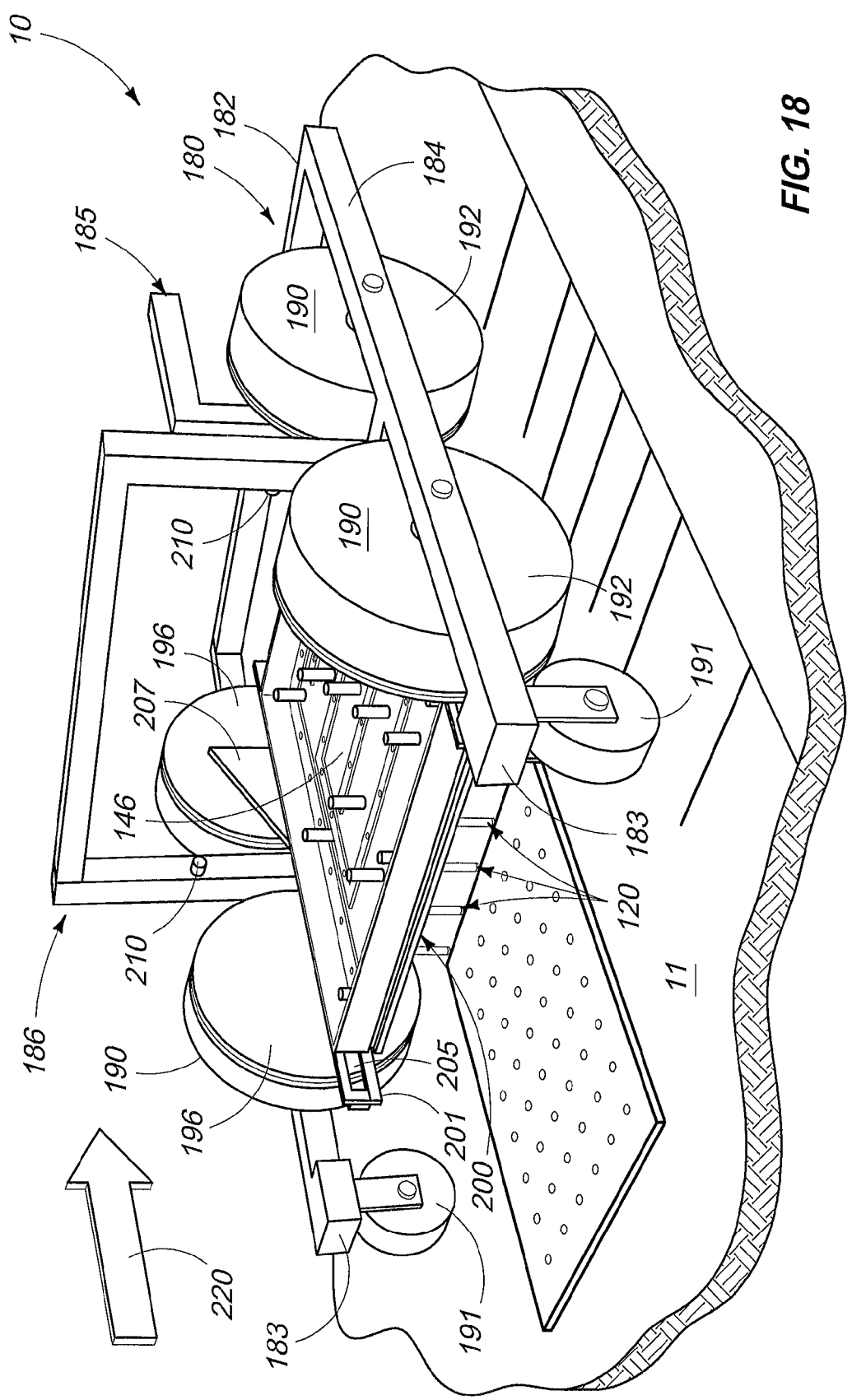
FIG. 18 is a fragmentary, perspective, side elevation view of the present invention, and which shows the earth traversing vehicle, which forms a feature of the present invention, located in yet another position along the course of travel, and after having treated a given soil area.

Referring now to the drawings (FIG. 13) it will be seen that an engagement post 210 is made integral with each of the transversely disposed and vertically extending platform guidance members 186. The respective engagement posts 210 each extend laterally, inwardly relative to the lateral frame members 184, and are operable to cooperate and engage the rail engagement surface 207, and which extends angularly upwardly from the upwardly facing surface 206 of the respective first and second rail members 201 and 202 respectively. The earth traversing vehicle 180 is moved in a given direction along a path of movement 220, and over the soil treatment area 11, in the manner as described hereinafter, and as seen in FIG. 1. As noted earlier, the earth traversing frame or carriage 181 incorporates or employs four earth engaging wheels 190, and which are mounted to the supporting frame 181. The area between the earth engaging wheels 190 is open to accommodate the accompanying moveable platform 140, and the non-conductive support members 146, bearing the electrodes 120, in a given electrode array, so as to allow movement of the electrode array or individual electrodes 120, upwardly and downwardly, towards the soil treatment area 11. The wheels 190 which are employed are standard wheel/tires which are typically found on car or truck trailers, and which are between 13 and 17 inches in diameter, and which further have a center hole, and 4 or 5 stud holes not shown. The wheels 190 are mounted on the supporting frame 181 via the axle 195 in the arrangement as seen in the drawings. As illustrated, a ridged disc 196 is typically manufactured from aluminum, and has a roller bearing, not shown, and which is mounted adjacent to the inside facing surface 194 of the respective earth engaging wheels. Individual platform engaging posts 197 are made integral with or are affixed to this rigid or aluminum disc 196. Again the platform movement assembly 200 (FIG. 11) including the first and second rail numbers 201 and 202 are positioned therebetween the wheels 190, and the individual platform engaging posts 197 are received in the respective channels 205, and which are defined by the first and second rail members 201 and 202, respectively. As should be understood, as the wheels 190 rotate, when they are moved across the soil treatment area 11, this rotation of the wheels 190 causes the platform 140, and non-conductive support member 146, to move downwardly with the platform engaging pins or posts 197, towards the soil treatment area 11. As should be understood, the weight of the apparatus 10 will force the electrodes 120 into the soil to be treated 11. As will be understood the wheels 190 do not stop moving. Therefore, continuous rotation of the wheels 190 will then pick up the electrode array as the platform engaging pins or posts 197 move upwardly as the respective wheels 190 continue to rotate. The respective platform engaging posts 197 are offset from the center of the wheels 190 so as to utilize the wheel rotation to provide upward and downward movement, as well as forward travel for the non-conductive support member 146, when the electrodes 120 are not inserted in the soil 11. The distance between the individual platform engaging posts 197 from the center of the wheel 190 is determined by the size of the electrode array of the non conductive support member 146. This further determines the distance needed to be covered or traversed from the removal, to the insertion of the individual electrodes 120, into the underlying soil treatment area 11. For example, in one possible example, if the soil treatment area 11 is approximately 24 inches in length, the accompanying moveable platform and electrode array 120 will need to move 28 inches to treat the next adjoining section of soil. In this spatial arrangement, this requires a 4½ inch drive or individual platform engaging post 197, offset, as measured, from the wheel center to achieve this distance in one rotation of the wheels 190, as provided. Important to the success of the apparatus 10 is the channel 205 in which the individual platform engaging posts 197 move while the electrodes 120 are in contact or inserted within the soil treatment area 11. As should be understood, roller bearings, not shown, and which are positioned on the individual platform engaging posts 197 travel in the channel 205, and allows the non conductive support member 146 to remain stationary in the soil location as the individual wheels 190 rotate, and further facilitates the vertical movement of the electrodes 120 As should be understood, as the electrodes 120 are inserted vertically into the soil, and then are removed, vertically, by the movement of the platform, when the non-conductive support member 146 moves upwardly and downwardly in response to the rotation of the earth engaging wheels 190, the underlying soil surface 11 is not substantially disturbed. This is best seen in FIGS. 1 and 18, respectively, and where a multiplicity of apertures, 300 appear in the soil which has been previously treated. These apertures were formed by the respective electrodes, 120. As should be understood, once the electrodes 120 are removed from the soil treatment area 11, the rail engaging surface 207 contacts the engagement post 210 which typically has a stationary rolling bearing mounted thereon. As the non-conductive support member 146 is lifted up by the individual platform engaging posts 197, and which is simultaneous with the movement of the wheels rotation 190, the respective engagement posts 210 come into contact with the rail engagement surface 207 thus applying a forward movement which is translated to the non-conductive support member 146. This causes the entire non-conductive support member 146, including platform 140, to move in a forward direction towards the proximal end 182, of the supporting frame 181.

Figure 12:
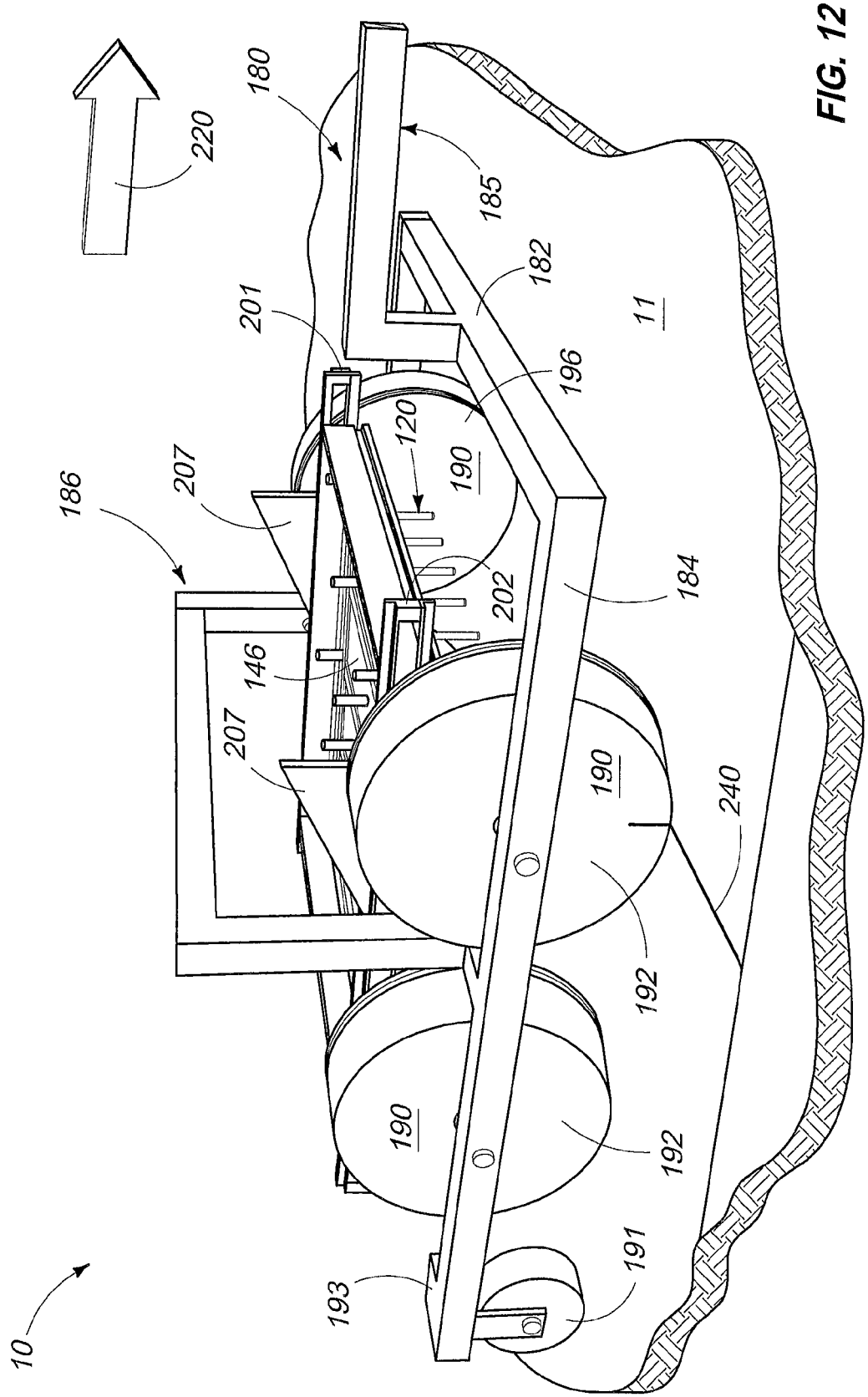
FIG. 12 is a fragmentary, perspective, side elevation view of an earth traversing vehicle carrying a movable platform in a first position, and which forms a feature of the present invention.
Figure 13:
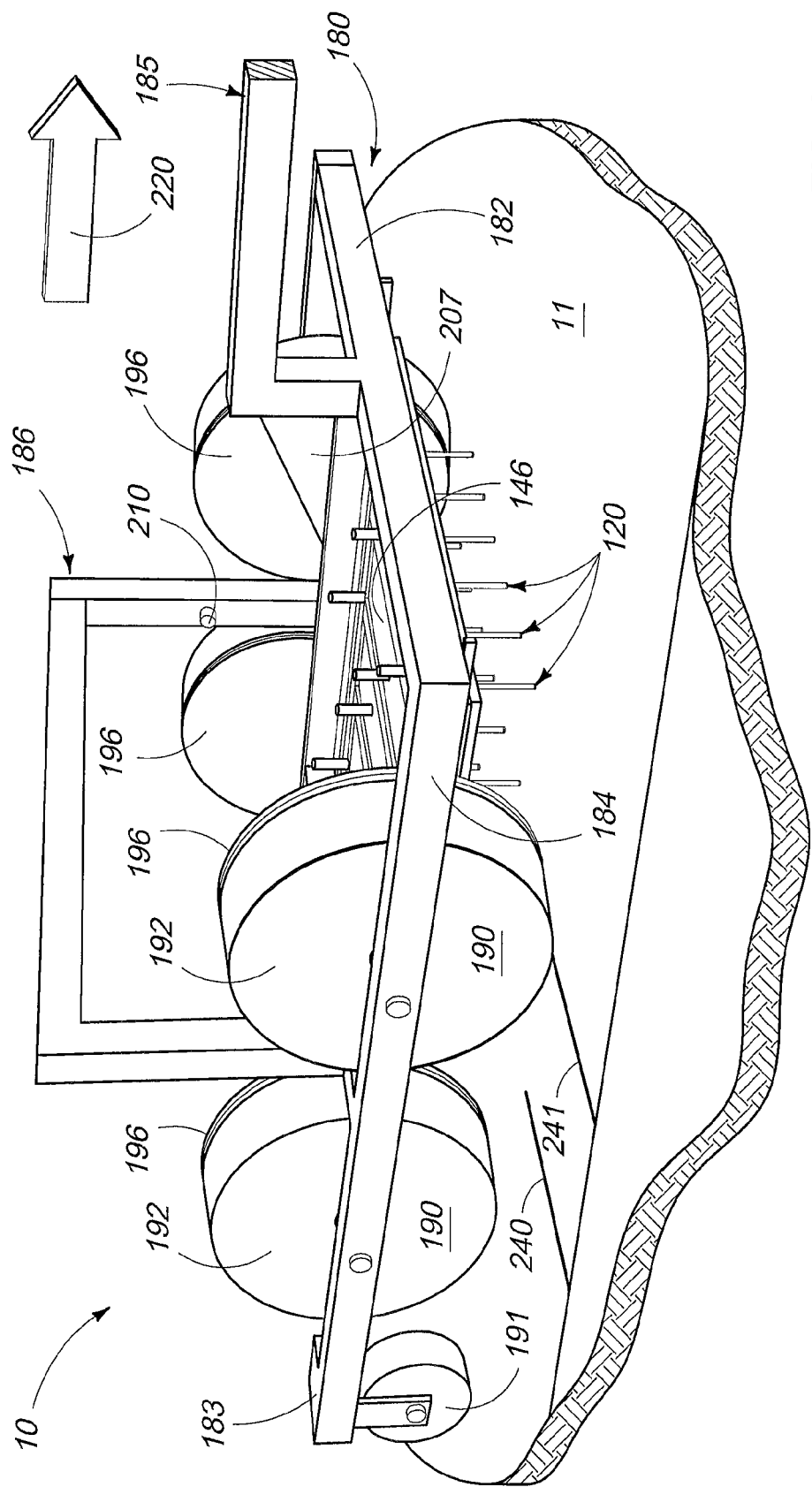
FIG. 13 is a fragmentary perspective, side elevation view of an earth traversing vehicle in a second position, and which forms a feature of the present invention, and which is further shown in a position where it has been advanced along a course of travel, over a soil treatment area.

Referring now to FIG. 12 and following, four positions of the movement of the non-conductive support member, 146, carrying the plurality of electrodes 120 during the sequence of one rotation of the wheels 190 is illustrated. Referring now to FIG. 12, it will be seen that the plurality of electrodes 120 which are located or disposed within a predetermined, spaced, electrode array is illustrated as being carried by the earth traversing vehicle 180, and located above the surface of the earth. The non-conductive support member 146, which is carried by the platform movement assembly 200 is located in a forward orientation on the individual first and second rail members 201 and 202 respectively, and the respective electrodes 120 are positioned to be inserted in the soil as the wheels 190 rotate the individual platform engaging posts forward and then downwardly towards the soil treatment region 11. As seen in FIG. 13, the distance traveled by the earth traversing 180 from a first starting position A, 240, to a second position B, 241 in this example is about 9.5 inches. With regard to FIG. 13, it will be recognized that the electrodes 120 have moved to, and have contacted the soil treatment area 11. As earlier discussed, the weight of the apparatus 10 is such that the downward force of the rotating individual platform engaging posts 197 which cooperate with the first and second rail members 201 and 202 is of a sufficient magnitude that the individual electrodes 120 are forced into the soil treatment area 11 in a substantially vertical path of travel. As the wheels 190 continue to rotate with only the individual platform engaging posts downwardly directed force acting on the non-conductive support member 146 by means of the first and second rail members 201 and 202, respectively it will be recognized that the forward force of the earth traversing vehicle 180 is now isolated within the individual first and second rail members 201 and 202 respectively.

Figure 14:
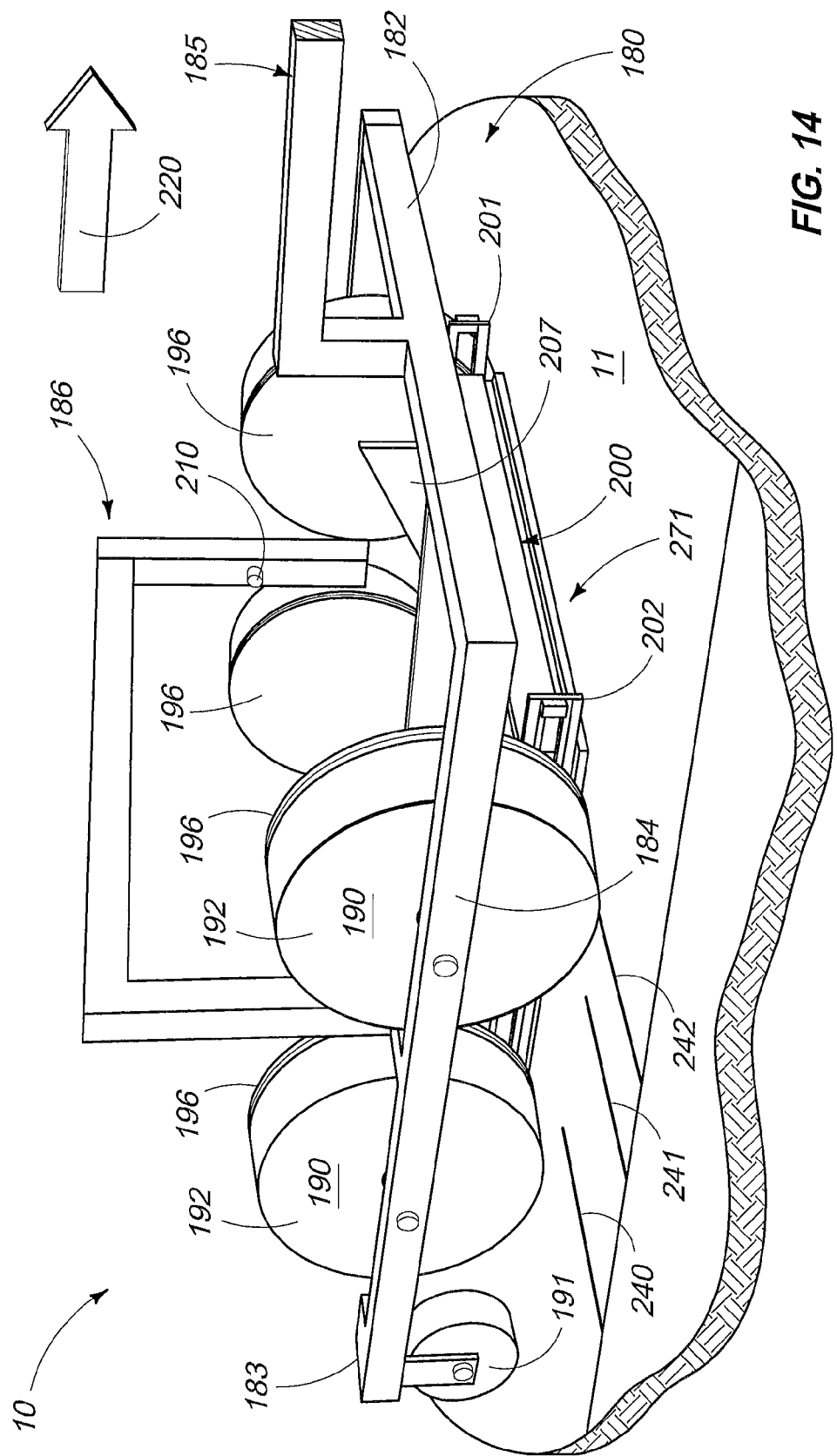
FIG. 14 is a fragmentary, perspective, side elevation view showing an earth traversing vehicle in a third position, and which forms a feature of the present invention, and which is further shown in a location further advanced along the course of travel from that seen in FIG. 11.

Referring now to FIG. 14, it will be recognized that when the earth traversing vehicle 180 reaches a third position C, and which is labeled by the numeral 242, that the individual electrodes 120 are fully inserted in the soil treatment area 11, and the accompanying methodology 10 for the treatment of the soil to manage a soil pest 12 is now being applied. As should be appreciated when the wheels 190 continue to rotate, the individual platform engaging posts 197 remain isolated within the individual first and second rail members 201 and 202, while the acting force transitions from downward motion to upward or lifting motion as the wheels 190 continue their respective rotation.

Figure 15:
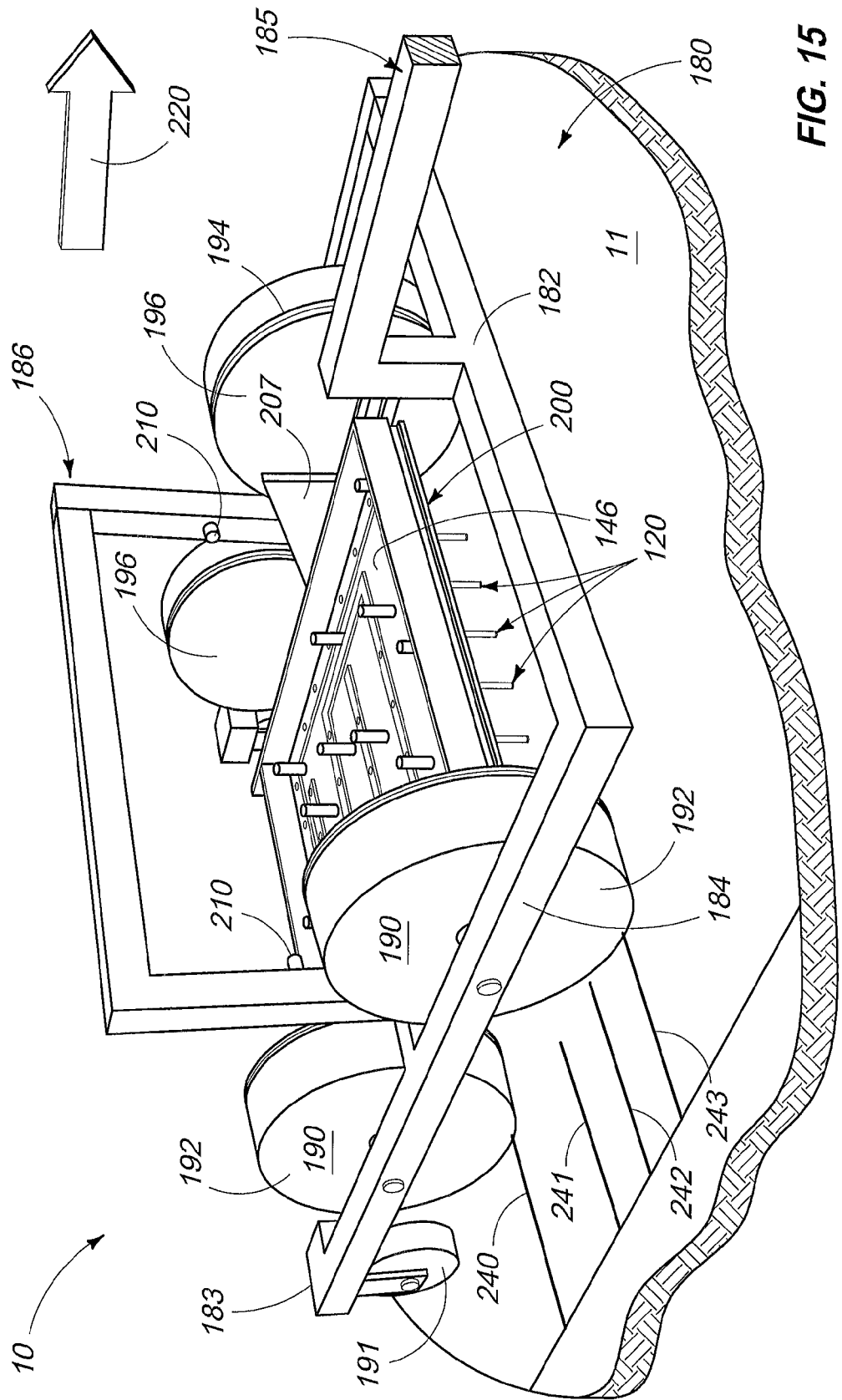
FIG. 15 is a fragmentary, perspective, side elevation view of an earth traversing vehicle in a fourth position, and which forms a feature of the present invention, and which is further shown in yet still another, further advanced position from that seen in FIG. 14.
Figure 16:
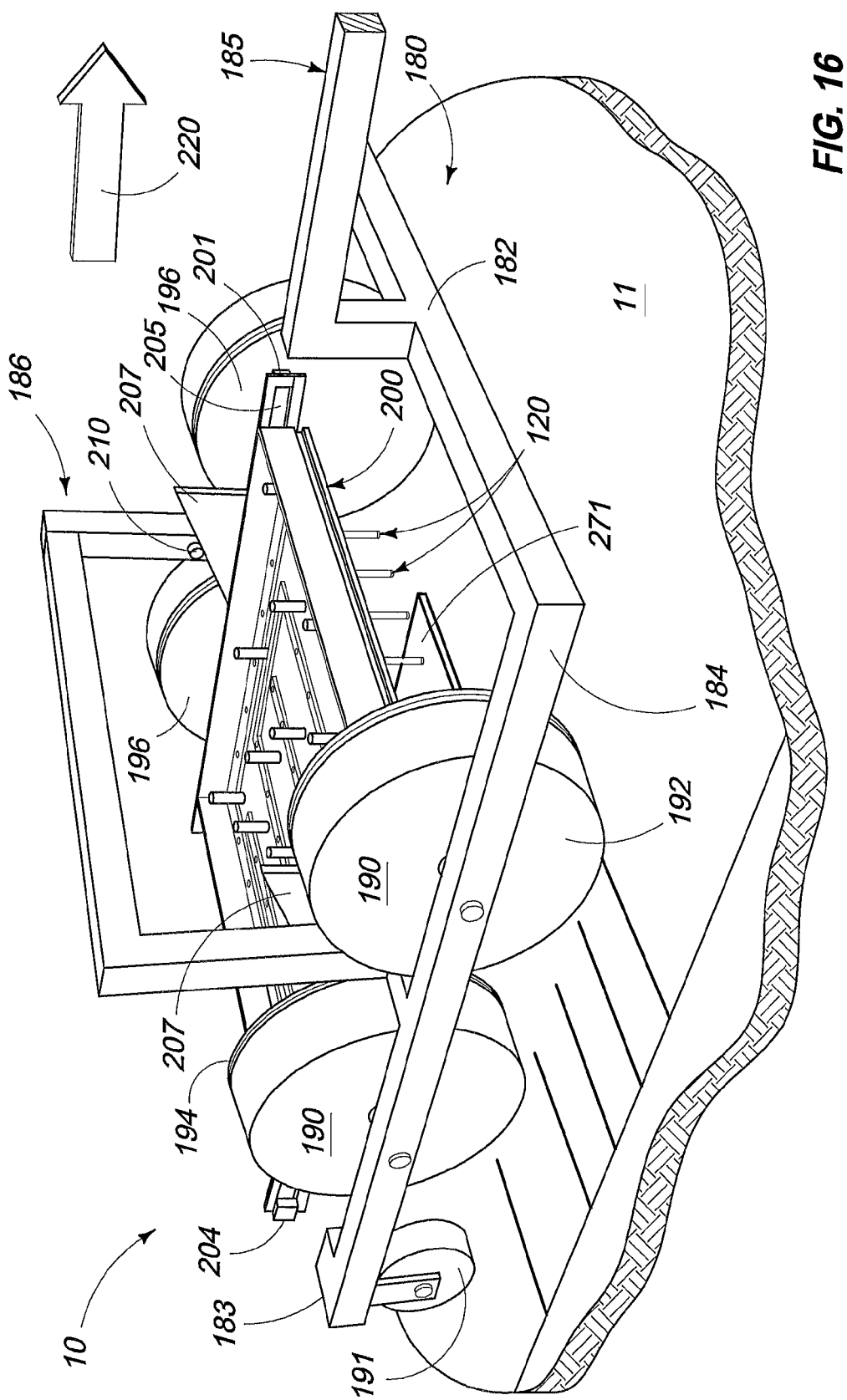
FIG. 16 is a fragmentary, perspective, side elevation view of an earth traversing vehicle in a fifth position, and which forms a feature of the present invention, and which is further shown in still another, advanced position relative to that seen in FIG. 15.
Figure 17:
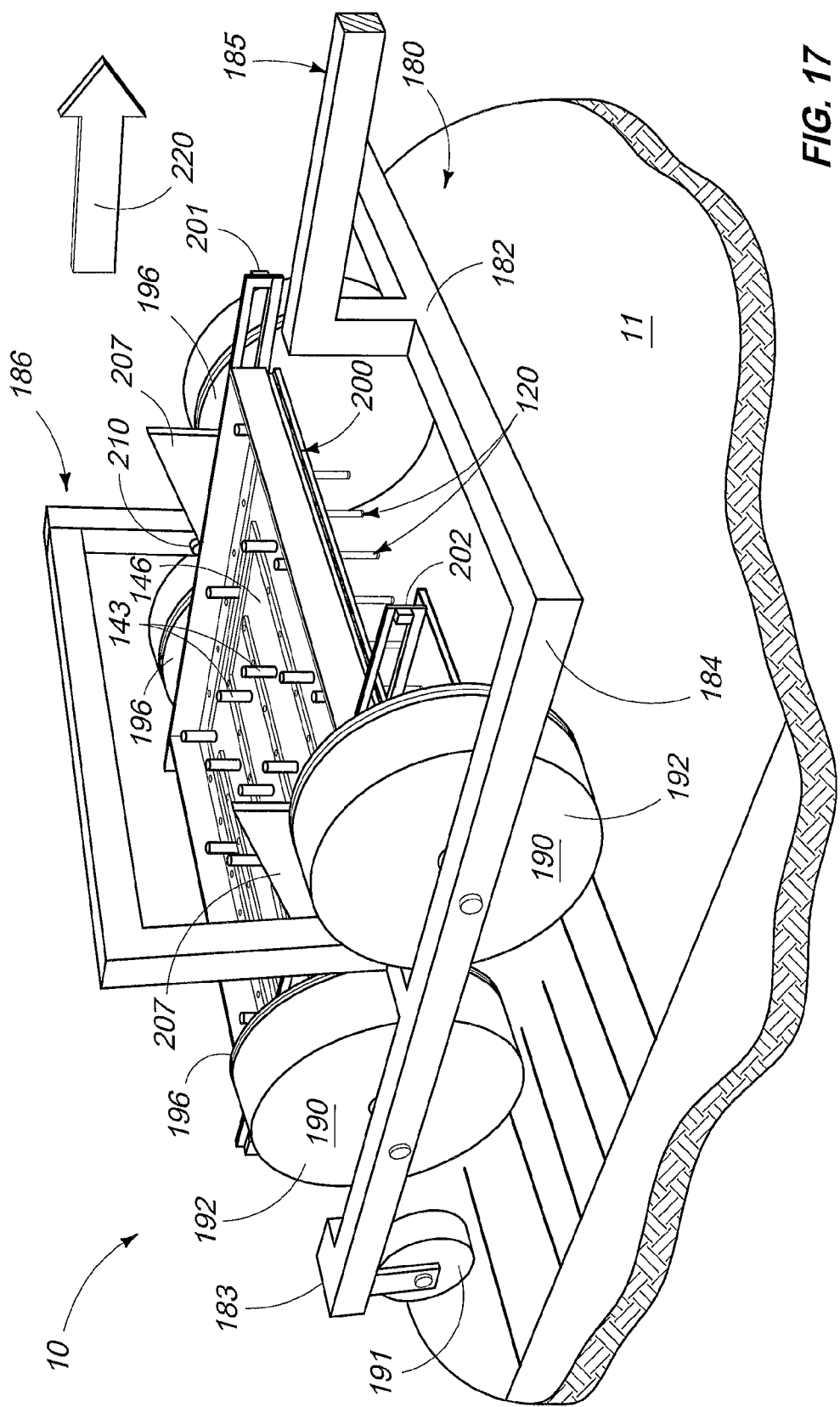
FIG. 17 is still another, fragmentary, perspective, side elevation view of the present invention, and which shows an earth traversing vehicle in still another position which is advanced along the course of travel.

Referring now to FIG. 15, and when the wheels 190 are at position D, and which is indicated by the numeral 243, the non-conductive support member 146 has been lifted substantially straight or vertically, upwardly, by the upward force exerted on the first and second rail members 201 and 202 by the individual platform engaging posts 197 which transmit the upward force of the rotating wheels 190. Therefore, the electrodes 120 are no longer in contact with the underlying soil 11. As should be understood, the isolated forward motion of the wheels 190 has caused the individual platform engaging posts 197 to move forward within the channel 205 of the respective first and second rail members 201 and 202 respectively, travel of the individual platform engaging posts 197 in the channel 205 occurs while the electrodes 120 remain in contact with the soil. In other words, the wheels 190 have moved 9 inches further than the non-conductive support member 146 which first carried the electrodes 120 into the soil region to be treated 11. As should be understood, the continued movement of the wheels 190, while the individual platform engaging posts 197 lift the non-conductive support member 146 to the top of the rotation of the wheels 190, subsequently causes the non-conductive support member 146 to be moved or propelled to a forward most position on the individual first and second rail members 201 and 202 respectively (FIGS. 16 and 17). During this portion of the wheel rotation 190, the engagement posts, 210, engage the rail engagement surface 207. This has the effect of forcibly moving the non-conductive support member 146 back to the forward most position on the first and second rail members 201 and 202 respectively. As should be appreciated, this sequence is repeated until the apparatus 10 reaches the end of the soil treatment area 11, in one direction (FIG. 1). Thereafter, the lifting arrangement 27, and which is installed on the tractor 25, and which is further propelling the earth engaging vehicle or carriage 180 along the soil treatment area 11, lifts the earth traversing vehicle 180, off of the soil treatment area 11. This lifting action takes the drive wheels 190 out of driving contact or engagement with the underlying earth, and allows the apparatus 10 to be moved or repositioned without the non-conductive support member 146 further moving upwardly and downwardly relative to the supporting frame 181. The apparatus 10 is then positioned or relocated in an untreated soil area 11, and the methodology as described, herein resumes. This process is repeated until the desired agricultural area 280 is treated.

As seen in FIG. 1, the source of high voltage electricity 13; isolation transformer 20; high voltage switching power supplies 30; and pulse control and wave form monitoring unit 60, voltage control unit 50, as well as the controller 80 may be positioned or carried by the tractor 25, or on a separate moveable vehicle located in close proximity to the apparatus 10 (not shown). As should be appreciated the power source 13 may be stationary or mobile with appropriately sized electrical cables connected to the various electrical assemblies as described earlier in this application. It should be understood that the dwelling time for the electrical pulse 130 treatment, that is, the time that the electrodes 120 are located in electrical transmitting relation relative to the soil treatment area 11, is controlled, at least in part, by the speed of the apparatus 10 as it moves across the face of the earth. As will be understood, the distance between the bottom and top of the vertical path of movement, where the individual platform engaging posts 197 carry the non-conductive support member 146, will affect the length of time which it takes to transition from inserting the electrodes, 120, and then lifting the non-conductive support member 146. Thus the electrodes, 120, will remain longer in the soil treatment area 11. This allows an additional "tuning" of the dwelling time during which the electrodes 120 are discharging pulses of electricity 130 as will be described, hereinafter, to control the soil pest 12 within the soil treatment area 11. As should be understood, longer length electrodes will require longer first and second rail members 201 and 202, respectively, so as to ensure that all the forward force of the vehicle 180 is isolated while the electrodes are in contact with the soil 11. In this situation, it should be appreciated that a larger diameter rotation for the individual earth engaging wheels 190 is also needed so as to provide clearance for the longer electrodes 120, and a longer longitudinal treatment dimension on the electrode array will be incorporated to ensure there is no untreated area in a given treatment region 280 (FIG. 1).

As described in the paragraphs, above, a method and apparatus for the management of a soil pest, and which is generally indicated by the numeral 10 is described. In the methodology of the present invention, and in its broadest aspect, the method includes a first step of providing a source of high voltage electricity having a predetermined capacitance, and which is generally indicated by the numeral 13. Still further the method includes a second step of electrically coupling the source of high voltage electricity 13 having the predetermined capacitance with the soil location 11 having a soil pest 12, which requires management. In its broadest aspect the method further includes a third step of supplying the source of high voltage electricity 13 having the predetermined capacitance to the soil location 11 in a predetermined number of pulses 130 to effect an in-situ management of the soil pest 12 at the soil location 11. As should be understood, the step of providing the high voltage electricity 13 having the predetermined capacitance comprises generating a source of high voltage DC electricity 13 having a voltage range of about 1 kV to about 100 kV; an amperage of about 50 amps to about 50 kA; and a frequency of about 1 Hz to about 100 Hz. This step further includes a step of providing a capacitance of about 1 uF to about 1,000 uF. In the methodology 10 of the present invention, the step of electrically coupling the source of high voltage electricity 13 having the predetermined capacitance further compromises providing a plurality of spaced the electrodes 120, having a given length dimension, and inserting the plurality of spaced the electrodes 120 into the soil location 11 to a predetermined depth. It should be understood that the source of high voltage electricity having the predetermined capacitance 13 is electrically coupled with at least some of the spaced electrodes 120.

In the methodology as described above, the step of providing the plurality of spaced electrodes 120 further comprises selecting a predetermined spacing of the respective electrodes 120 which facilitates a transmission of the source of high voltage electricity 13 having the predetermined capacitance across the soil location 11 having the soil pest 12 requiring management, and between at least some of the plurality of electrodes. It should be understood that the transmission of the high voltage electricity having the predetermined capacitance 13 between at least some of the electrodes 120 affects a neurological system possessed by the soil pest 12 which is to be managed. In the methodology as described, the step of supplying the source of high voltage electricity having the predetermined capacitance 13 to the soil location 11 in the predetermined pulses 130 further comprises selecting an application time during which the respective pulses 130 are applied of about 0.1 seconds to about 60 seconds to affect a desired management of the soil pest 12. As noted above, the soil pest 12 to be managed has a neurological system which generates a neurological response when exposed to the pulses of high voltage electricity 130 having the predetermined capacitance, and which is delivered to the soil location 11. As should be understood, prior to the step of selecting an application time to affect a desired management of the soil pest 12, the method 10 further comprises determining an electrical conductivity of the soil location 11, and which has the soil pest 12 requiring management; and selecting a neurological response to be affected by the application time of the high voltage electricity having the predetermined capacitance 13 so as to facilitate the management of the soil pest 12 at the soil location 11. In the methodology as described, the soil conductivity of the soil location 11 lies within a range of about 100 to about 2,500 Micro Siemens per cubic centimeter of soil at the soil location 11.

The soil pest 12 to be managed is selected from the group comprising Tylenchomorpha Nematodes; Diptherophorina Nematodes; and Dorylaminda Nematodes; and the selected neurological response of the soil pest 12 to be managed, and which is affected by the pulses of high voltage electricity 130 having the predetermined capacitance comprises a motility; a sensory and/or autonomic response of the soil pest 12. In the methodology 10 as described above, the step of supplying the source of high voltage electricity having the predetermined capacitance 13 to the soil location 11, and in predetermined pulses 130 to effect the management of the soil pest 12 at the soil location 11 further comprises delivering to the soil location 11 greater than about 2 Joules of electricity per cubic centimeter of soil at the soil location 11 so as to facilitate a reduction in an adverse soil pest effect at the soil location of greater than about 5%. In the present application, the adverse soil pest effect at the soil location 11 comprises a root galling and/or root infestation of a plant which is planted at the soil location 11 by an action of the soil pest 12. As should be understood, the adverse soil pest effect decreases a plant vigor; a plant crop yield; and/or lowers the production quality of the plant which is affected by the soil pest 12 at the soil location 11, and where the plant is being grown.

In the arrangement as shown in the drawings, and in the implementation of the methodology as noted above, the plurality of spaced electrodes 120 are located at a distance of about 4 centimeters to about 20 centimeters, one from another; and the respective electrodes 120 have a length dimension of about 4 centimeters to about 40 centimeters respectively. In the methodology of the present invention, the step of supplying the source of high voltage electricity having the predetermined capacitance 13 to the soil location 11 further compromises providing at least 1 high voltage DC solid state electrical switch 100 and which, when rendered electrically closed, allows the passage of the source of high voltage electricity having the predetermined capacitance 13, and a high current to the soil location 11. Further, and when the electrical switch is rendered electrically open, the high voltage solid state electrical switch 100 substantially stops the passage of the high voltage electricity having the predetermined capacitance 13, and high currents, to the soil location 11. The method 10 further comprises providing a multiplicity of capacitors 90 which are selectively electrically coupled with the high voltage DC solid state electrical switch 100. It should be understood that the high voltage DC solid state electrical switch 100 is electrically coupled with at least one of the capacitors 90, and wherein the high voltage DC solid state electrical switch 100 when rendered electrically closed facilitates an electrical discharge of at least one of the capacitors 90. In the arrangement as described, the step of providing the source of high voltage electricity having the predetermined capacitance comprises generating a source of electricity and delivering the source of the generated electricity to at least one of the electrically discharged capacitors 90. It should be understood that the respective capacitors store the high voltage electricity having the predetermined capacitance 13 by way of the action of the high voltage DC solid state electrical switch 100 when the high voltage DC solid state switch is rendered electrically open.

In the methodology as described above, the multiplicity of capacitors 90 each respectively have a discharge rate which is calculated as an elapsed time which is needed to electrically discharge any previously stored electrical power in the respective capacitors 90 by way of the action of the high voltage DC solid state electrical switch 100, and subsequently form a pulse of high voltage electricity 130 having the predetermined capacitance, and which is delivered to the soil location 11. The step of forming a pulse of high voltage electricity 130 having a predetermined capacitance by electrically discharging each capacitor 90 is accomplished at a discharge rate of about 100 microseconds to about 500 milliseconds during a time interval which is less than about 100 times per second.

In the methodology 10 as described, a surge current is immediately generated upon the rendering of the high voltage DC solid state electrical switch 100 electrically closed, and the electrical discharge of the previously electrically charged capacitor 90, and wherein the methodology further comprises the step of generating a surge current of about 50 Amps to about 2,000 Amps immediately following the step of rendering the high voltage DC electrical switch 100 electrically closed. In the present methodology 10, the method as described 10 further comprises providing an isolation transformer 20 which is electrically coupled with both the source of high voltage electricity having a predetermined capacitance 13, and with a plurality of spaced electrodes 120 which are inserted into the soil location 11 having the soil pest 12 which need to be managed; and operating the isolation transformer 20 in a manner so as to effect a transmission of the high voltage electricity having the predetermined capacitance 13 through the soil location 11, and between adjacent electrodes 120, and to further impede the dissipation of the high voltage electricity having the predetermined capacitance 13 into the soil at the soil location 11. In the arrangement as seen in the drawings, and in the present methodology as earlier described, at least some of the plurality of spaced electrodes 120, have a different electrical polarity.

To determine the efficacy and criticality of the operational ranges of the present invention, the inventors performed numerous trials. From this testing data the inventors scaled an appropriately sized apparatus for implementing the methodology. In this regard, the inventors first used a square acrylic testing cell which was approximately 1 centimeter deep and 5 centimeter both high and wide. With this test cell, cooper electrodes which were approximately 5 centimeter long, and 1 centimeter wide, were placed on opposite sides of the test cell and were connected to the earlier mentioned apparatus 10 by way of copper contacts. The test cell was then filled with tap water as a conductive medium, and repeated tests were performed to refine the wave form of the pulse 130, and to assure circuit stability before beginning trials. Oscilloscopes and voltage meters, as well as high voltage probes monitored the load across the test cell, and further monitored the discharge rates of the capacitors 90, and the pulse rate of the computer controlled signal generator. In the earliest trials the electrical discharges were limited to 2 KV [DC] and which were stored in a 4 uF, 5 KV capacitor 90, and which was subsequently pulsed at a rate of 20 Hz, so as to deliver about 160 Joules per second. This electrical energy resulted in about 6.4 Joules per cubic centimeter per second of electrical power delivered to the test cell. In the earliest trials, Nematodes extracted from infested soil, and suspended in solution were placed in the water filled square acrylic test cell, and the energy profile as recited, above, was applied. In a trial performed on Oct. 12, 2013, treatments of 2 KV [DC] pulsed at 20 Hz were applied for 2.5; 5 and 10 seconds, respectively. This pulsing and time duration equated to 400, 800 and 1600 Joules, or 16, 32 or 64 Joules per cubic centimeter of solution. In this earlier testing, cucumber sprouts which are referred to, hereinafter, as "assays" were inoculated with treated samples having nematodes. The assays were allowed to grow for a period of 4 weeks alongside a control which was inoculated with untreated samples from the same batch of Nematodes and solution. After 4 weeks the roots of the cucumber "assays" were rinsed, and the galls, which are a universal measurement of the Nematodes population, were counted or otherwise "scored." Galling on the control roots were measured at approximately an 80% to 90% galling. On the other hand, galling scoring on sample assays that were treated for 10 seconds showed 5% galling after having received an electrical dosage equal to 64 Joules per cubic centimeter. Galling scoring on specimens that received the pulsing which resulted in 32 Joules per cubic centimeter showed galling of about 20%, and specimens that had been exposed to 16 Joules of electricity per cubic centimeter showed a galling equal to about 30%.

Similar results were achieved when trials with Nematode infested soil was used instead of water as the Nematode medium in the square acrylic test cell. Using soil from a tomato plant infested with M. Chitwoodi Nematodes, the subsequent treatment of the test cell which received 2 KV [DC] and which were pulsed at 20, 30 and 40 Hz were applied for periods of 10, 20 and 40 seconds, respectively. This resulted in electrical dosages of 128, 192 and 256 Joules per cubic centimeter of soil being applied. After 3 weeks the assay roots were rinsed, and the galls scored, as earlier discussed. With regard to the controls, the roots showed approximately 80% galling. For those specimens that were pulsed, and which received an electrical dosage of about 128 Joules per square centimeter of soil at 20 Hz, and 20 seconds, the roots showed 5% galling. Further, those test assays which received a dosage of 256 Joules per cubic centimeter at 20 Hz, for 40 seconds, had roots which showed only 30% galling. On the other hand, those test roots that had received a dosage of 192 Joules per cubic centimeter, at 30 Hz, for 20 seconds, had roots which showed 20% galling. Those test roots which were exposed to 128 Joules per cubic centimeter of soil, and 40 Hz, for 10 seconds showed 0% galling. Finally, for those roots that had received an electrical dosage of 256 Joules per cubic centimeter of soil, at 40 Hz for 20 seconds had roots which showed 0% galling. The inventors believed that these were surprising results that further proved the efficacy of the methodology in soil.

Subsequent trials using the present invention 10 served to scale the method closer to a usable size. Moving now from the previously mentioned 25 cubic centimeter test cell, to a circular test cell, the inventors increased the treatment area, and volume, and moved to further refine the efficiency of the energy profile which was being delivered in order to achieve the benefits of the present invention. During this testing, a total volume for the circular test cell was about 31.4 cubic centimeters. In this arrangement, a center, electrically conductive pin, and an outer ring electrode configuration was employed. The electrodes spacing remained the same. Therefore, the same amount of energy could be applied, but to a larger volume of water or soil. In a trial performed on Nov. 20, 2013, again, Nematodes previously extracted from infested soil, and suspended in solution, were placed in the water filled circular test cell. Using the same cucumber assay procedure as mentioned above, the subsequent results which were generated, again, were consistent with those as observed using the square test cell. In this testing, 2 KV [DC], at a pulse of 20 and 30 Hz was applied for periods of 5 seconds; 3 seconds; and 1 second, respectively. This delivered electrical power in the amount of 50.96 Joules per cubic centimeter; 15.3 Joules per cubic centimeter, 5.1 Joules per cubic centimeter; and 2.55 Joules per cubic centimeter respectively. In this testing, the capacitor as used varied between 12 uF and 4 uF. This testing showed that the controls had roots where 80% galling resulted. For those assays which were exposed to 2.55 Joules per cubic centimeter of electricity (1 KV at 20 Hz for 1 second with 4 uF) these assays showed galling similar to the controls. For those assays which received 5.1 Joules per cubic centimeter of electrical power (2 KV at 20 Hz for 1 second 4 uF) the roots showed galling of about 70%. Another assay, which received 15.3 Joules per cubic centimeter, resulted in only 40% galling. An analysis of all the data received showed that those assays receiving electrical current in the amount of 50.96 Joules per cubic centimeter (2 KV at 20 Hz for 5 seconds, 12 uF) had roots which had 0% galling. The inventors have theorized, based on this information, that increased capacitance had a greater impact than originally thought in the elimination or impeding of subsequent Nematode infestations.

In one of the first usages of the current invention, 4 pin electrodes which were spaced 5 centimeter apart, and oriented in a square-like arrangement was configured to have a third 4 uF/5 KV capacitor. Therefore a total of 12 uF was used to treat plant pots containing 125 cubic centimeters of infested soil at that time. A trial was performed on Dec. 19, 2013 and used soil from a tomato plant infested with M. Chitwoodi Nematodes. This infested soil was distributed into the pots and the treatment which was applied was 2 KV [DC], and which was pulsed at 20 Hz, and which further was applied for 2.5; 5; 10; 15; 20 and 30 seconds, respectively. When the results were obtained, the control plants showed roots having galling in an amount equal to about 80%. For those specimens that received electrical pulses equal to of about 76.8 Joules per cubic centimeter, and 20 seconds duration, 0% galling was observed. For those specimens receiving 38.4 Joules per cubic centimeter, and 10 seconds of treatment, 5% galling was observed. For those roots that had received 57.6 Joules per cubic centimeter of electricity, and 15 seconds of treatment, 0% galling was evident. For those specimens receiving 19.2 Joules per cubic centimeter, and 5 seconds of treatment, 10% galling was observed. For those plants receiving 115 Joules per cubic centimeter of electricity, and 30 seconds of treatment, 0% galling was observed. Interestingly, one specimen that had received 9.6 Joules per cubic centimeter, and 2.5 seconds of treatment, showed galling which was 200-300% greater than the control. This was indeed a very surprising result. These results appear to indicate that the application of electrical power in this range elicited a hatch response from the Nematode eggs present in the infested soil. This was an important achievement to the inventors inasmuch as the inventors were able to pinpoint one region in the range of electricity that was delivered, and which is necessary to elicit a hatch response. This is an important discovery inasmuch as the initiation of a hatch response, in fallow soil, could lead to further control of the soil pest 12 because those Nematodes hatched in this manner could potentially starve to death before the soil could be planted with a plant. This would inhibit the infection of the plants subsequently planted.

In addition to the foregoing, another trial was performed on Dec. 19, 2013, and focused on the Soybean Cyst Nematode and which was extracted from infested soil and suspended in a solution that was subsequently distributed into sterile soil, and then treated with the methodology of the present invention. The present invention was configured with 3 capacitors (12 uF), and a resulting treatment of 2 KV [DC] was applied at pulses of 20 Hz, for time periods of 5; 10; 15; and 20 seconds, respectively. Using the same methodology as the cucumber assay procedure, as earlier discussed, the results proved the efficacy of the method. It should be understood that the Soybean Cyst Nematode is a particularly difficult Nematode to effect or treat because of the resilient outer shell of the cyst which contains the target eggs. To achieve any noteworthy effect would surpass any previous attempts that are known. The aforementioned electrical treatment which was applied to the test cell demonstrated the effectiveness of the present invention by reducing the number of cysts per gram of root that was subsequently analyzed. For example, control plants typically had 100 cysts per gram of root. Whereas, for those plants exposed to the electrical treatment which resulted in a dosage of 76.8 Joules per cubic centimeter of soil (20 second treatment), only 25 cysts per gram of root were found. For those assays receiving a dosage of 38.4 Joules per cc (15 second treatment), a complete population collapse was observed and which is believed due to the treatment. Further, for those plants that received a treatment of 57.6 Joules per cubic centimeter of soil, 75 cysts per gram of root were observed. Further, for those plants that received an electrical treatment of 19.2 Joules per cubic centimeter, (5 seconds of treatment), only 20 cysts per gram of root was observed.

In another series of tests, the present methodology was used to determine a damage threshold for a plant root system. Using the above mentioned 2 KV [DC] which was applied with a capacitor delivering 12 uF of electrical power, at pulses to 20 to 60 Hz, and then applied in dwelling times up to 60 seconds, this electrical energy was delivered to both sod samples, and small lemon cypress tress in an attempt to harm the plants. After several weeks of observation, only the samples treated with the highest frequencies for the longest dwelling times showed any sign of damage. The damage is believed to be caused primarily by the excessive heat which is generated by the aforementioned electrical delivery. The results suggest that the methodology can be applied to plants and the soil without concern for damaging the plants, providing, however, that a relatively short dwelling time is utilized. One of the surprising results in the testing which was observed by the inventors is that while early tests were conducted with 4 electrodes which had a target spacing of about 5 centimeters, the inventors expanded the electrode array in order to include more electrodes. What surprised the inventors was that as the number of electrodes 120 increased, the discharge rate for the apparatus became shorter with the addition of each electrode. With a shorter discharge rate, the apparatus 10 was allowed more time to recharge. This period of rest between discharges was important to maintain the remaining components in an operational state, and to prevent the buildup of excessive heat in the respective components.

The early trials conducted by the inventors were substantially fixed at about 2 kV of electrical power, but the inventors varied the frequency [Hz], capacitance [uF], and dwell time as measured in seconds, that were employed to establish that an effective range for impeding or controlling the aforementioned soil pests lied in a range of about 2 Joules per cubic centimeter of soil up to 256 Joules. This critical range provides a target for scaling any resulting apparatus to what is achievable for a device which is employed in various agricultural applications. In constructing and deploying an appropriate apparatus, care must be taken to maintain the effective electrical dose, that is, the Joules per cubic centimeter, by way of selecting, and then balancing all of the following: generating and applying more electrical energy; incorporating more efficient components in a delivery apparatus; and reducing the dwell time, that is, the amount of time during the delivery of the electrical pulses, and for making the conductive medium (soil) more electrically conductive.

To continue the exploration of the efficacy of the present methodology, the inventors did testing regarding the use of the pulses of electricity 130 as applied to earthworms as described below. In this regard, it should be understood that earthworms are beneficial in agriculture. However in the case of the golf and turf industries, they are a nuisance. The earthworm trial served to demonstrate the effect of the electrical pulses 130 which were applied to a soil location containing earthworms. The treatments ranged from about 1.9 Joules per second, to about 75 Joules per second. The results were surprising, but yet not unexpected based upon the earlier research. In the very first application of the treatment prior to the beginning of the trial cycle, the application of 1 pulse of electricity which was equal to 1.5 kV at 8 uF was sufficient to stun an earthworm which was placed in water. Although the earthworm revived in a few minutes it was outlived by a considerable margin by the control earthworms which were utilized in the test. This result was consistent across the treatment spectrum. The control worms survived several days, while the longest surviving and previously treated worm survived less than 24 hours. Those worms exposed to a longer treatment time survived a shorter period of time than those exposed to a shorter treatment time. All the trials performed with the earthworms were performed with 2 capacitors, each having a capacity for 4 uF. Earthworms were placed in both soil, and then later in water, and then were subsequently exposed to 1.5 kV at 20 Hz for selected time periods 5; 2 and 1 second, respectively, and which received 9.6; 3.8 and 1.9 Joules of electricity respectively. In a second test, which was performed in soil, the earthworms were exposed to 2 kV at 20 Hz, and which received electrical pulses for durations of 30 seconds; 10 seconds; 5 seconds; and 2 seconds respectively. In this test, the earthworms were exposed to 76.8; 25.6; 12.8 and 5.12 Joules respectively. In a third test which was conducted in water, the earthworms were exposed to 1.5 kV, at 20 Hz, for time periods of 5 seconds; 2 seconds; and 1 second, respectively. The earthworms received during these time periods 38; 15.3; and 7.6, Joules of electricity, respectively. Again, survival of the earthworms was proportional to the dosage of electricity received.

The inventors performed further tests on wax worms which served as an analog for pests with similar physiology such as grubs for which interest is quite high in the turf industry. In this regard, the inventors observed similar responses to the treatment as the earthworms described above, although not as dramatic. The inventors observed that, rather than hours, it took wax worms several days to die while the controls took nearly a week. As with the earthworms, the wax worms exposed to longer treatments of electricity survived a shorter period of time, while those with shorter treatment times lived longer. The controls outlived all of the treated worms. These trials and others within the ranges discussed proved the efficacy of the methodology and the criticality of the ranges as earlier described in this application.

Operation

The operation of the described embodiment of the present invention is believed to be readily apparent is briefly summarized at this point. An apparatus for managing a soil pest, and which implements the present methodology as previously described includes as a first matter, a source of high voltage electricity having a predetermined capacitance 13; and an isolation transformer 20 which is electrically coupled with the source of the high voltage electricity having the predetermined capacitance 13. The apparatus for implementing the methodology includes a plurality of spaced electrodes 120 which are located in electrical contact with a soil location 11, and which has a soil pest 12 to be managed. The isolation transformer 20 is electrically coupled to the respective spaced electrodes 120. The apparatus for implementing the methodology includes a capacitor 90 which is electrically coupled with a source of high voltage electricity having a predetermined capacitance 13, and with the plurality of spaced electrodes 120. The capacitor 90 can store the source of high voltage of electricity having the predetermined capacitance 13, and subsequently discharge the previously stored high voltage of electricity having the predetermined capacitance to the plurality of spaced electrodes 120. The apparatus to implement the present methodology includes a high voltage electrical switch 100, and which is electrically coupled to the capacitor 90, and which further can be rendered electrically opened, or closed, in a predetermined manner so as to produce a predetermined electrical pulse 130 which is electrically transmitted to the respective plurality of spaced electrodes 120, and across the soil location 11. The electrical pulse 130 delivers at least about 2 Joules of electricity per cubic centimeter of soil, and which is located at the soil location, and between the respective plurality of spaced electrodes 120 so as to facilitate a management of the soil pest 12.

The apparatus 10 as employed to implement the methodology as earlier described includes, in one form of the invention a plurality of spaced electrodes 120 which have different electric polarities. In the arrangement as illustrated, the isolation transformer 20 facilitates the controllable transmission of the electrical pulse 130 through the soil 12, and at the soil location 11, and between the plurality of spaced electrodes 120 and further impedes the electrical pulses 130 from substantially electrically dissipating into the soil location. In the arrangement as seen in the drawings, and which implements the methodology, the high voltage electrical switch 100 comprises a SCR/thyristor. As noted above, the plurality of electrodes are oriented in a predetermined array which can be readily moved from a first soil location 271 to a second soil location 272 (FIG. 1) in a repeating manner, so as to treat a given agricultural area 280. In the arrangement as seen in the drawings, the plurality of spaced electrodes 120 are located at a distance of about 4 centimeters, to about 20 centimeters, one relative to the others. Each electrode 120 has a length dimension of about 4 centimeters to about 40 centimeters. In the arrangement as seen in the drawings, the apparatus for implementing the methodology includes a controller 80 which senses a soil conductivity of the soil location 11. The controller 80 is electrically coupled with a source of electricity having the predetermined capacitance 13, and with a high voltage electrical switch 100. The controller 80 adjustably controls the generation of the electrical pulses 130 based upon the detected soil conductivity, so as to facilitate the delivery of the at least 2 Joules of electricity per cubic centimeter of soil that is located between the electrodes 120 which have been inserted in the soil location 11.

As earlier noted, the source of high voltage electricity having the predetermined capacitance 13 has a voltage range of about 1 kV to about 100 kV; an amperage of about 50 Amps to about 50 kA; a frequency of about 1 Hz to about 100 Hz; and a capacitance of 1 uF to about 1,000 uF.

The apparatus for implementing the methodology 10 of the present invention produces or generates a multiplicity of electrical pulses 130 which are generated and transmitted to the soil location 11. The respective electrical pulses are delivered to the soil location at a predetermined frequency, and are further applied for a time period of about 0.1 to about 60 seconds. As seen in the drawings, the apparatus delivers electrical pulses 130 to the soil location 11 in a range of about 2 Joules to about 250 Joules of electricity per cubic centimeter of soil at the soil location 11, and to a soil depth of less than about 40 centimeters. The delivery of the electrical pulses 130 facilitates the management of the soil pest 12 at the soil location 11. In the arrangement, as earlier described, the respective electrical pulses 130 are generated over a time period of about 100 microseconds to about 500 microseconds. In the arrangement as previously described, the respective electrical pulses 130 are generated at less than about 100 times per second. In the present invention, the high voltage electrical switch 100, when rendered electrically closed, is effective in electrically discharging at least one of the capacitors 90, and immediately generating a surge current of about 50 Amps to about 2,000 Amps.

The apparatus for implementing the methodology of the present invention 10 includes a high voltage electrical switch 100 which comprises a multiplicity of high voltage electrical switches which are individually associated with each of the respective plurality of capacitors 90. The apparatus further comprises an electrical switch driver 255/256 which is operably associated with each of the high voltage electrical switches 100 and which is further operable to render the respective high voltage electrical switches 100 electrically open, and closed, so as to affect the generation of the electrical pulses 130. The apparatus further includes a controller 80 which is operably coupled to each of the respective electrical switch drivers 255/256 via control board 260.

In the arrangement as seen in the drawings, the apparatus for implementing the present methodology 10 includes an electrical bus 150, and 151 respectively, and which are electrically coupled in electrical current receiving relation relative each to the capacitors 90, and are disposed in electrical current discharging relation relative to each of the electrodes 120. In the arrangement as seen in the drawings, the respective spaced electrodes 120 have opposite first and second ends 122 and 123 respectively. The first end 122 of each electrode 120 is supported on an electrically nonconductive support member 146, in a predetermined spaced arrangement, so as to form an array of electrodes 120 which individually extend outwardly from the support member 146. The electrodes are further inserted into the soil at the soil location 11, and further the electrical bus 150 and 151, respectively, is electrically coupled to the first end of each of the electrodes 120 so as to deliver the generated pulse of high voltage electricity 130 into the soil location 11 by way of the plurality of electrodes 120.

The apparatus for implementing the methodology 10 further comprises an earth traversing vehicle 180 which is supported for rolling engagement over the soil location 11 having the soil pest 12 to be managed. The earth traversing vehicle has a vertically movable non-conductive support member 146 which is borne by the earth traversing vehicle 180, and which is movable along a path of travel 220 from a first position, 240, where the non-conductive support member 146 is disposed in spaced relation relative to the soil location 11; to a second position, 241, and where the non-conductive support member 146 is located adjacent to the soil location 11. The plurality of electrodes 120 which are mounted on or made integral with the non-conductive support member 146, are then inserted into, and subsequently withdrawn from the soil location 11, by the vertical movement of the non-conductive support member 146, as the non-conductive support member 146 moves between the first and second positions 240 and 241, respectively. The non-conductive support member 146 moves between the first and second positions 240 and 241, as the earth traversing vehicle 180 continues to move over the soil location 11. It should be understood that the non-conductive support member 146, carrying the plurality of electrodes 120, remains motionless, and in contact with the soil location 11 for a predetermined time period (dwelling time) as the earth traversing vehicle 180 remains in motion over the soil location 11.

The soil location to be treated 11 typically comprises a narrowly elongated soil location (FIG. 1) having a given surface area, and which is located within a larger cultivated agricultural area 280 which has the soil pest 12 that needs management. The earth traversing vehicle 180 sequentially inserts and then withdraws the plurality of electrodes 120 which are borne by the non-conductive support member 146 in a fashion so as to facilitate a resulting treatment of the entire surface area of the narrowly elongated soil location 11 to effect the management of the soil pest 12, and while minimally disturbing the soil location as the plurality of electrodes 120 are repeatedly inserted into and then withdrawn from the soil location by the vertical movement of the moveable non-conductive support member 146 as effected by the continuous movement of the earth traversing vehicle 180.

The methodology of the present invention is more specifically described below. In this regard the method of the present invention 10 includes, as a first step, providing a source of high voltage electricity 13; and also providing a plurality of spaced electrodes 120 each having a given length dimension, and which are oriented in a predetermined spaced relationship one relative to the other. The plurality of spaced electrodes are oriented in a given pattern and are positioned in electrical discharging relation relative to a soil location 11 having a soil pest 12 to be managed. The method includes another step of providing a capacitor 90, and which is electrically coupled with the source of high voltage electricity and storing the source of high voltage electricity in the capacitor so as to form a source of high voltage electricity having a predetermined capacitance 13. The methodology includes another step of providing a high voltage solid state electrical switch 100 which is electrically coupled with the source of high voltage electricity having the predetermined capacitance 13, and which further is stored in the capacitor 90. The method further includes another step whereby the high voltage solid state electrical switch 100 is further electrically coupled with each of the spaced electrodes 120. In the present methodology the high voltage solid state electrical switch 100 can be rendered electrically opened so as to facilitate a storage of the source of high voltage of electricity in the capacitor 90; and electrically closed, so as to facilitate an electrical discharge of the capacitor 90, and the subsequent delivery of the source of high voltage electricity having the predetermined capacitance 13 to the respective plurality of electrodes 120. The method includes another step of providing an electrical switch driver 255/256 which is electrically coupled with the high voltage solid state electrical switch 100. The switch driver 255/256, when actuated, is effective in causing the high voltage solid state electrical switch 100 to be rendered either electrically open or electrically closed. The methodology includes another step of providing an isolation transformer 20 which is electrically coupled with both the source of the high voltage electricity having the predetermined capacitance 13, and with the plurality of spaced electrodes 120, and which are oriented in electrical discharging relation relative to the soil location 11; and controlling the operation of the isolation transformer 20 in a manner so as to effect a transmission of the high voltage electricity having the predetermined capacitance 13 through the soil location 11, and between the adjacent spaced electrodes 120, and to further impede the dissipation of the high voltage electricity having the predetermined capacitance into the soil, at the soil location 11. The method includes another step of providing a controller 80 which is coupled in controlling relation relative to the electrical switch driver 255/256, and which is effective in rendering the high voltage solid state electrical switch 100 electrically opened, and closed. The method includes another step of repeatedly rendering the electrical switch driver 255/256 operable to facilitate an electrical opening and closing of the high voltage solid state electrical switch 100, and so forming a multiplicity of pulses of electricity 130 which are delivered to the plurality of electrodes 120, and which are oriented in electrical discharging relation relative to the soil location 11. The plurality of electrical pulses 130 which are generated facilitate a reduction in an adverse soil pest effect at the soil location 11 of greater than about 5%.

In the methodology as described above, the step of providing a source of high voltage electricity further comprises supporting a mobile electric power generating assembly 290 on an earth traversing vehicle 25 for movement across the soil location having a soil pest 12 requiring management (FIG. 1); and generating the source of high voltage electricity with the mobile electric power generation assembly 290. With regard to the methodology as described, the step of providing the plurality of spaced electrodes 120 further comprises operably coupling the plurality of spaced electrodes 120 on an earth traversing carriage 180, and moving the plurality of electrodes across the soil location having the soil pest 12 to be managed. The earth traversing carriage 180 moves the respective spaced electrodes 120 vertically into, and out of the soil location 11. In the methodology as described, earlier, the step of providing the plurality of spaced electrodes 120 comprises providing a plurality of individual electrodes having a given length dimension, and positioning the individual electrodes 120 in a predetermined, spaced array; and then inserting the plurality of electrodes 120 having the given length dimension to a predetermined depth in the soil location 11 having the soil pest 12 to be managed.

In the methodology as described, the step of providing the spaced electrodes 120 further comprises providing a movable, non-conductive support member 146 on an earth traversing carriage 180; moveably coupling the non-conductive support member 146 on the earth traversing carriage; mounting the spaced electrodes 120 on the movable non-conductive support member 146; propelling the earth traversing carriage 180 across the soil location 11; and moving the non-conductive support member 146 mounting the spaced electrodes 120, along a vertically disposed path of travel so as to repeatedly insert, and then withdraw the electrodes 120 from the soil location 11 having the soil pests to be managed 12 for a predetermined period of time [dwelling time] to facilitate the reduction in the adverse soil pest effect at the soil location 11.

In the methodology as described, the adverse soil pest effect at the soil location 11 comprises root galling and/or root infestation of a plant which is planted at the soil location 11 by an action of the soil pest 12. The adverse soil pest effect decreases a plant vigor; a crop yield; and/or lowers a production quality of the plant which is affected by the soil pest 12 at the soil location 11. In the methodology as described above, the step of forming the multiplicity of pulses of electricity 130 further comprises selecting a pulse application time during which the respective electrical pulses 130 are applied to the soil location 11, and which lies in a range of about 0.1 seconds to about 60 seconds to effect the desired management of the soil pest 12. In the methodology as described above, and before the step performing the multiplicity of pulses of electricity 130, the method further comprises determining an electrical conductivity of the soil location 11, and which has the soil pest 12 requiring management; and selecting a neurological response of the soil pest 12 to be affected by the application time of the respective electrical pulses 130 delivered to the soil location 11. In the methodology as described, the step of determining the electrical conductivity of the soil comprises orienting a sensor in electrical conductive sensing relation relative to the soil location 11; and coupling the sensor in a signal transmitting relation relative to the controller 80. The step of providing the controller 80 further comprises adjustably controlling the electrical switch driver 255/256 with the controller 80 so as to produce resulting electrical pulses 130 to effect the desired management of the soil pest 12 at the soil location 11.

Therefore, it will be seen that the present method and apparatus for the management of a soil pest 12 provides a convenient means for reducing an adverse soil pest effect on plants that are planted in an agricultural region 280 in a manner not possible heretofore. The present methodology, and the apparatus which is utilized to implement same, is convenient to utilize, is environmentally friendly, and provides a convenient means for treating large regions of agricultural production land in a manner not possible heretofore. The present methodology and apparatus provide surprising results in view of the long felt need to control soil pests which have such a devastating affect on various crops that are planted both domestically and worldwide.

In compliance with the statute, the invention has been described in language more or less specific as to structural and methodical features. It is to be understood, however, that the invention is not limited to the specific features shown and described since the means herein disclosed comprise preferred forms of putting the invention into effect. The invention is therefore, claimed in any of its forms or modifications within the proper scope of the appended claims appropriately interpreted in accordance with the Doctrine of Equivalence.

The invention claimed is:

1. A method for the management of a soil pest, comprising:

providing a source of high voltage DC electricity having a voltage range of about 1 kV to about 100 kV; an amperage of about 50 amps to about 50 kA; a frequency of about 1 Hz to about 100 Hz; and a predetermined capacitance of about 1 uF to about 1000 uF;

electrically coupling the source of high voltage DC electricity having the predetermined capacitance with a soil location having a soil pest which requires management, and wherein the soil location has a soil conductivity which lies within a range of about 100 to about 2500 Micro Siemens per cubic centimeter of soil at the soil location; and wherein the step of electrically coupling the source of high voltage electricity having the predetermined capacitance further comprises providing a plurality of spaced electrodes having a given length dimension, and inserting the plurality of the spaced electrodes into the soil location to a predetermined depth, and wherein the source of high voltage DC electricity having the predetermined capacitance is electrically coupled with at least some of the spaced electrodes, and wherein the step of providing the plurality of spaced electrodes further comprises selecting a predetermined spacing of the respective electrodes which facilitates a transmission of the source of high voltage DC electricity having the predetermined capacitance across the soil location having the soil pest requiring management, and between at least some of the plurality of electrodes, and wherein the transmission of the high voltage DC electricity having the predetermined capacitance between at least some of the electrodes effects a neurological system possessed by the soil pest which is to be managed; and supplying the source of high voltage DC electricity having the predetermined capacitance to the soil location in a predetermined number of pulses to effect an in-situ management of the soil pest at the soil location, and wherein the step of supplying the source of the high voltage DC electricity further comprises the step of selecting an application time during which the respective pulses are applied to the soil location of about 0.1 seconds to about 60 seconds to effect the desired in-situ management of the soil pest, and wherein the soil pest to be managed has a neurological system which generates a neurological response when exposed to the pulses of high voltage DC electricity having the predetermined capacitance, and which is delivered to the soil location, and wherein, prior to the step of selecting an application time to effect a desired in-situ management of the soil pest, the method further comprises determining an electrical conductivity of the soil location which has the soil pest requiring in-situ management; and selecting a neurological response to be effected by the application time of the high voltage DC electricity having the predetermined capacitance so as to facilitate the in-situ management of the soil pest at the soil location.

2. A method as claimed in claim 1, and wherein the soil pest to be managed is selected from the group comprising Tylenchomorpha Nematodes; Diptherophorina Nematodes; and Dorylaminda Nematodes; and the selected neurological response of the soil pest to be managed, and which is effected by the pulses of the high voltage electricity having the predetermined capacitance comprises a motility; a sensory and/or an autonomic response of the soil pest.

3. A method as claimed in claim 1, and wherein the step of supplying the source of high voltage DC electricity having the predetermined capacitance to the soil location, and in predetermined pulses to effect the management of the soil pest at the soil location further comprises, delivering to the soil location greater than about 2 joules of electricity per cubic centimeter of soil at the soil location so as to facilitate a reduction in an adverse soil pest effect at the soil location of greater than about 5 percent.

4. A method as claimed in claim 3, and wherein the adverse soil pest effect at the soil location comprises a root galling and/or root infestation of a plant which is planted at the soil location, by an action of the soil pest, and wherein the adverse soil pest effect decreases a plant vigor; a crop yield; and/or lowers a production quality of the plant which is effected by the soil pest at the soil location, and where the plant is being grown.

5. A method as claimed in claim 1, and wherein the plurality of spaced electrodes are located at a distance of about 4 centimeters to about 20 centimeters one, from the others, and wherein each of the electrodes have a length dimension of about 4 centimeters to about 40 centimeters.

6. A method as claimed in claim 1, and wherein the step of supplying the source of the high voltage DC electricity having the predetermined capacitance to the soil location further comprises providing at least one high voltage DC solid state electrical switch, and which, when rendered electrically closed, allows the passage of the source of the high voltage DC electricity having the predetermined capacitance, and a high electrical current, to the soil location, and wherein, when the electrical switch, when rendered electrically open, substantially stops the passage of the high voltage DC electricity having the predetermined capacitance, and high electrical current, to the soil location; and wherein the method further comprises providing a multiplicity of capacitors which are selectively, electrically coupled with the high voltage DC solid state electrical switch, and wherein the high voltage DC solid state electrical switch is electrically coupled with at least one of the capacitors, and wherein the high voltage DC solid state electrical switch, when rendered electrically closed, facilitates an electrical discharge of at least one of the capacitors.

7. A method as claimed in claim 6, and wherein the step of providing the source of the high voltage DC electricity having the predetermined capacitance comprises generating a source of DC electricity; and delivering the source of the generated electricity to at least one electrically discharged capacitor, and wherein the discharged capacitor stores the high voltage DC electricity having the predetermined capacitance by way of the action of the high voltage DC solid state electrical switch when the high voltage DC solid state electrical switch is rendered electrically open.

8. A method as claimed in claim 7, and wherein the multiplicity of capacitors each respectively have an electrical discharge rate which is calculated as an elapsed time which is needed to electrically discharge any previously stored electricity in the respective capacitors by way of the action of the high voltage DC solid state electrical switch, and subsequently form a pulse of high voltage DC electricity having the predetermined capacitance, and which is delivered to the soil location, and wherein the method further comprises forming a pulse of high voltage DC electricity having a predetermined capacitance, by electrically discharging each capacitor at an electrical discharge rate of about 100 microseconds to about 500 millisecond during a time interval which is less than about 100 times per second.

9. A method as claimed in claim 8, and wherein a surge current is immediately generated upon the rendering of the high voltage DC solid state electrical switch electrically closed, and the discharge of a previously electrically charged capacitor, and wherein the methodology further comprises a step of generating a surge current of about 50 Amps to about 2000 Amps immediately following the step of rendering the high voltage DC electrical switch electrically closed.

10. A method as claimed in claim 1, and wherein the method further comprises providing an isolation transformer which is electrically coupled with both the source of high voltage DC electricity having a predetermined capacitance, and with the plurality of spaced electrodes which are inserted into the soil location having the soil pests which need to be managed; and operating the isolation transformer in a manner so as to effect a transmission of the high voltage DC electricity having the predetermined capacitance through the soil location, and between adjacent electrodes, and which impedes at least in part, the dissipation of the high voltage DC electricity having the predetermined capacitance into the soil at the soil location.

11. An apparatus configured to implement the method of claim 1.

12. A method as claimed in claim 10, and wherein at least some of the plurality of spaced electrodes have a different electrical polarity.

13. A method for the management of a soil pest, comprising:
providing a source of high voltage electricity;
providing a plurality of spaced electrodes each having a given length dimension, and which are oriented in a predetermined, spaced relationship, one relative to the other, and orienting the spaced electrodes in electrical discharging relation relative to a soil location having a soil pest to be managed;
providing a capacitor and which is electrically coupled with the source of the high voltage electricity, and storing the source of the high voltage electricity in the capacitor so as to form a source of high voltage electricity having a predetermined capacitance;

providing a high voltage solid state electrical switch which is electrically coupled with the source of high voltage electricity having the predetermined capacitance, and which is stored in the capacitor, and wherein the high voltage solid state electrical switch is further electrically coupled with each of the spaced electrodes, and wherein the high voltage solid state electrical switch can be rendered electrically open so as to facilitate a storage of the source of high voltage electricity in the capacitor, and electrically closed so as to facilitate an electrical discharge of the capacitor and the subsequent delivery of the source of the high voltage electricity having the predetermined capacitance to the respective plurality of spaced electrodes;

providing an electrical switch driver which is electrically coupled with the high voltage solid state electrical switch, and wherein the high voltage solid state electrical switch, when actuated, is effective in causing the high voltage solid state electrical switch to be rendered either electrically open, or electrically closed;

providing an isolation transformer which is electrically coupled with both the source of the high voltage electricity having the predetermined capacitance, and with the plurality of spaced electrodes which are oriented in electrical discharging relation relative to the soil location, and operating the isolation transformer in a manner so as to effect a transmission of the high voltage electricity having the predetermined capacitance through the soil location, and between the adjacent spaced electrodes, and to impede, at least in part, the dissipation of the high voltage electricity having the predetermined capacitance into the soil at the soil location;

providing a controller which is coupled in controlling relation relative to the electrical switch driver, and which is effective in rendering the high voltage solid state electrical switch electrically opened and closed; and repeatedly rendering the electrical switch driver operable to facilitate an electrical opening and closing of the high voltage solid state electrical switch and so forming a multiplicity of pulses of electricity which are delivered to the plurality of electrodes, and which are oriented in electrical discharging relation relative to the soil location, and wherein the plurality of electrical pulses facilitate a reduction in an adverse soil pest effect at the soil location of greater than about 5%.

14. A method as claimed in claim 13, and wherein the step of providing a source of high voltage electricity further comprises supporting a mobile electric power generating assembly on an earth traversing vehicle for movement across the soil location having the soil pest requiring management; and generating the source of the high voltage electricity with the mobile electric power generation assembly.

15. A method as claimed in claim 13, and wherein the step of providing the plurality of spaced electrodes further comprises mounting and operably coupling the plurality of spaced electrodes on an earth traversing vehicle, and moving the plurality of electrodes across the soil location having the soil pest to be managed, and wherein the earth traversing vehicle moves the respective spaced electrodes vertically into, and out of the soil location.

16. A method as claimed in claim 15, and wherein the step of providing the plurality of spaced electrodes comprises providing a plurality of individual electrodes having a given length dimension, and positioning the individual electrodes in a predetermined, spaced array; and inserting the plurality of electrodes having the given length dimension to a predetermined depth into the soil location having the soil pest to be managed.

17. A method as claimed in claim 16, and wherein the step of providing the plurality of individual electrodes having the given length dimension further comprises causing at least some of the individual electrodes to have a different electrical polarity.

18. A method as claimed in claim 15, and wherein the step of providing the spaced electrodes further comprises providing a moveable supporting platform on the earth traversing vehicle; moveably coupling the supporting platform on the earth traversing vehicle; positioning the spaced electrodes on the moveable platform; propelling the earth traversing vehicle across the soil location, and selectively moving the supporting platform, and which is carrying the spaced electrodes, along a vertically disposed path of travel so as to repeatedly insert, and then withdraw the electrodes from the soil location having the soil pest to be managed for a predetermined period of time so as to facilitate the reduction in the adverse soil pest effect at the soil location.

19. A method as claimed in claim 13, and wherein the adverse soil pest effect at the soil location comprises a root galling and/or root infestation of a plant which is planted at the soil location, by an action of the soil pest, and wherein the adverse soil pest effect decreases a plant vigor; a crop yield; and/or lowers a production quality of the plant which is effected by the soil pest at the soil location.

20. A method as claimed in claim 16, and wherein the plurality of spaced electrodes are located at a distance of about 4 centimeters to about 20 centimeters, one from the others, and wherein each of the electrodes have a length dimension of about 4 centimeters to about 40 centimeters.

21. A method as claimed in claim 13, and wherein the step of forming the multiplicity of pulses of electricity further comprises selecting an application time during which the respective electrical pulses are applied to the soil location, and which lies in a range of about 0.1 second to about 60 seconds to effect a desired management of the soil pest.

22. A method as claimed in claim 21, and wherein before the step of forming the multiplicity of pulses of electricity, the method further comprises determining an electrical conductivity of the soil location which has the soil pest requiring management; and selecting a neurological response of the soil pest to be effected by the application time of the respective electrical pulses to the soil location.

23. A method as claimed in claim 22, and wherein the step of determining the electrical conductivity of the soil comprises orienting a sensor in electrical conductive sensing relation relative to the soil location; and coupling the sensor in a signal transmitting relationship relative to the controller; and wherein the step of providing the controller further comprises adjustably controlling the electrical switch driver with the controller so as to produce resulting electrical pulses to effect the desired management of the soil pest at the soil location.

24. A method as claimed in claim 23, and further comprising delivering to the soil location greater than about 2 joules of electricity per cubic centimeter of soil, at the soil location, so as to effect the reduction of the soil pest effect of greater than 5%.

25. An apparatus configured to implement the method of claim 13.

* * * * *

UNITED STATES PATENT AND TRADEMARK OFFICE
CERTIFICATE OF CORRECTION

PATENT NO.         : 9,936,686 B2
APPLICATION NO.    : 14/462733
DATED              : April 10, 2018
INVENTOR(S)        : Jason D. Crisp, Ekaterini Riga and Gordon J. McComb It is certified that error appears in the above-identified patent and that said Letters Patent is hereby corrected as shown below:

On the Title Page

Item (73) Assignee - Replace "Lisi Globa, LLC, Richland, WA (US)" with --Lisi Global, LLC, Richland, WA (US)--

In the Specification

Column 6, Line 9 - Replace "science in useful art" with --science and useful arts--

Column 17, Line 6 - Replace "the electrodes 120" with --electrodes 120--

Column 19, Line 20 - Replace "cooper electrodes" with --copper electrodes--

Column 22, Line 9 - Replace "cypress tress" with --cypress trees--

Signed and Sealed this
Seventh Day of May, 2019

Andrei Iancu
*Director of the United States Patent and Trademark Office*